US009315830B2

(12) United States Patent
Walker et al.

(10) Patent No.: US 9,315,830 B2

(45) Date of Patent: Apr. 19, 2016

(54) METHOD OF PRODUCING A RECOMBINANT MICROORGANISM

(71) Applicant: LanzaTech New Zealand Limited, Auckland (NZ)

(72) Inventors: David Jeffrey Fraser Walker, Amherst, MA (US); Michael Koepke, Skokie, IL (US)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 14/608,132

(22) Filed: Jan. 28, 2015

(65) Prior Publication Data

US 2015/0211022 A1 Jul. 30, 2015

Related U.S. Application Data

(60) Provisional application No. 61/932,737, filed on Jan. 28, 2014.

(51) Int. Cl.
*C12N 15/66* (2006.01)
*C12N 15/90* (2006.01)

(52) U.S. Cl.
CPC .................................... *C12N 15/902* (2013.01)

(58) Field of Classification Search
None
See application file for complete search history.

(56) References Cited

U.S. PATENT DOCUMENTS

| | | | |
|---|---|---|---|
| 5,173,429 | A | 12/1992 | Gaddy et al. |
| 5,593,886 | A | 1/1997 | Gaddy |
| 6,368,819 | B1 | 4/2002 | Gaddy et al. |
| 2011/0117655 | A1 | 5/2011 | Tracy et al. |
| 2011/0229947 | A1 | 9/2011 | Zahn et al. |

FOREIGN PATENT DOCUMENTS

| | | | |
|---|---|---|---|
| WO | 0208438 | A2 | 1/2002 |
| WO | 2007117157 | A1 | 10/2007 |
| WO | 2008028055 | A2 | 3/2008 |
| WO | 2008115080 | A1 | 9/2008 |
| WO | 2009064200 | A2 | 5/2009 |
| WO | 2009151342 | A1 | 12/2009 |
| WO | 2010084349 | A1 | 7/2010 |
| WO | 2011112103 | A1 | 9/2011 |
| WO | 2012024522 | A2 | 2/2012 |
| WO | 2012026833 | A1 | 3/2012 |
| WO | 2012053905 | A1 | 4/2012 |
| WO | 2012112427 | A2 | 8/2012 |
| WO | 2012115527 | A2 | 8/2012 |
| WO | 2013036147 | A2 | 3/2013 |
| WO | 2013133882 | A2 | 9/2013 |
| WO | 2013180581 | A1 | 12/2013 |
| WO | 2013180584 | A1 | 12/2013 |
| WO | 2013185123 | A1 | 12/2013 |
| WO | 2013191567 | A1 | 12/2013 |
| WO | 2014036152 | A1 | 3/2014 |

OTHER PUBLICATIONS

International Search Report for International Patent Application PCT/US2015/013373, Korean Intellectual Property Office, Apr. 28, 2015.
Abrini, Arch Microbiol, 161: 345-351, 1994.
Al-Hinai, Appl Environ Microbiol, 78: 8112-8121, 2012.
Argyos, Appl Environ Microbiol, 77: 8288-8294, 2011.
Bruns, Appl Environ Microbiol, 69: 1980-1989, 2003.
Cartman, Appl Environ Microbiol, 78: 4683-4690, 2012.
Heap, J Microbiol Meth, 70: 452-464, 2007.
Heap, Nucleic Acids Res, 40: e59, 2012.
Herbert, FEMS Microbiol Lett, 229: 103-110, 2003.
Hungate, Methods Microbiol, 3B: 117-132, 1969.
Jennert, Microbiol, 146: 3071-3080, 2000.
Kast, J Mol Biol, 222: 99-124, 1991.
Keis, Int J Syst Evol Microbiol, 51: 2095-2103, 2001.
King, Nat Rev Microbiol, 5: 107-118, 2007.
Köpke, PNAS, 107: 13087-13092, 2010.
Köpke, Curr Opin Biotechnol, 22: 320-325, 2011.
Mermelstein, Biotechnol, 10: 190-195, 1992.
Murphy, Gene, 246: 321-330, 2000.
Murphy, J Bacteriol, 180: 2063-2071, 1998.
Murray, Microbiol Molec Biol Rev, 64: 412-434, 2000.
Ng, PLoS ONE, 8: e56051, 2013.
Parthasarathy, Development of a Genetic Modification System in Clostridium scatologenes ATCC 25775 for Generation of Mutants, Masters Project, Western Kentucky University, 2010.
Perez, Biotechnol Bioeng, 110: 1066-1077, 2012.
Pleiss, Curr Opin Biotechnol, 22: 611-617, 2011.
Quandt, Gene, 127: 15-21, 1993.
Ragsdale, Biochim Biophys Acta, 1784: 1873-1898, 2008.
Schiel-Bengelsdorr, Synthetic Biol, 15: 2191-2198, 2012.
Sharan, Nat Protoc, 4: 206-223, 2009.
Stratz, Appl Environ Microbiol, 60: 1033-1037, 1994.
Tanner, Int J Syst Bacteriol, 43: 232-236, 1993.
Tirado—Acevedo, Production of Bioethanol from Synthesis Gas Using Clostridium Ijungdahlii, PhD thesis, North Carolina State University, 2010.
Williams, J Gen Microbiol, 136: 819-826, 1990.
Wolfe, Adv Microbiol Physiol, 6: 107-146, 1971.
Olson, Methods Enzymol, 510: 317-330, 2012.

*Primary Examiner* — Jim Ketter
(74) *Attorney, Agent, or Firm* — Andrea E. Schoen

(57) ABSTRACT

The invention provides a genetic tool to insert, replace, delete, or otherwise manipulate a nucleic acid sequence in a microorganism to produce a recombinant microorganism. Notably, the invention makes use of homologous recombination, a type of genetic recombination in which nucleotide sequences are exchanged between two similar or identical molecules of DNA. Since the invention involves three homologous recombination events, it is referred to as a "triple cross" method.

18 Claims, 12 Drawing Sheets

SEQUENCE LISTING

<160> NUMBER OF SEQ ID NOS: 13

<210> SEQ ID NO 1
<211> LENGTH: 1032
<212> TYPE: DNA
<213> ORGANISM: Artificial sequence
<220> FEATURE:
<223> OTHER INFORMATION: Synthetic

<400> SEQUENCE: 1

```
atgaaaggag agtttaaaat gaaagaagaa ttaaaacaga taaaggaaaa tgcctttaac     60

gaattaaaaa ataaaaagtt agatatagag gatataagag ttaaatattt aggtaaaaag    120

ggagaactta caaaaatact caggggcatg aaggatcttt ccaaagaaga aagacctgca    180

attggtaagc ttgccaatga agtgaggagt acactggaaa atgctataga agaggcatca    240

aaaaagataa aatcaagtgc tatacaagca aagctgcaga atgaaacaat tgatattact    300

atgcctggca taaagcaaac tgtaggaaag cgccatccgc tagaacaaac actagaagag    360

atgaaacaga tatttatttc tatgggattt actatagaag aaggtcctga agtagagaag    420

gattattata actttgaagc acttaacata cctaaaaatc atccagcaag gggtgaacag    480

gataccttt atataaatga caatgtagtg cttagaactc aaacttctcc aatacaggta    540

agaactatgg aaaaacaaaa acccccaata aagatgatat ctccaggtaa agtttatcgt    600

tcagattcag tggatgctac tcattcacct atattttatc aaatggaagg cctagtagtt    660

gacaaaggta taacttttgc aaatttaaaa ggcactcttg aactatttgc taaaaagtta    720

ttcggaaatg acatacgtac aaaattcaga cctcatcatt tcccttttac agaaccttct    780

gcagaaatgg atgccagttg ctttgtatgc catggaaaag gctgcagagt atgtaaggga    840

gaagggtgga tagaactttt aggatgcgga atggttcatc ctcaggtact tagaaattgt    900

ggaatagatc ctgaagttta tagtggattt ggttttggaa tgggtgtaga taggatggtc    960

atgttaaaat acggaataga tgatataaga aacatgtatg aaagtgacat gagattttta   1020

aatcaatttt aa                                                       1032
```

<210> SEQ ID NO 2
<211> LENGTH: 343
<212> TYPE: PRT
<213> ORGANISM: Artificial sequence
<220> FEATURE:
<223> OTHER INFORMATION: Synthetic

<400> SEQUENCE: 2

```
Met Lys Gly Glu Phe Lys Met Lys Glu Glu Leu Lys Gln Ile Lys Glu
1               5                   10                  15

Asn Ala Phe Asn Glu Leu Lys Asn Lys Lys Leu Asp Ile Glu Asp Ile
            20                  25                  30

Arg Val Lys Tyr Leu Gly Lys Lys Gly Glu Leu Thr Lys Ile Leu Arg
        35                  40                  45

Gly Met Lys Asp Leu Ser Lys Glu Glu Arg Pro Ala Ile Gly Lys Leu
    50                  55                  60

Ala Asn Glu Val Arg Ser Thr Leu Glu Asn Ala Ile Glu Glu Ala Ser
65                  70                  75                  80

Lys Lys Ile Lys Ser Ser Ala Ile Gln Ala Lys Leu Gln Asn Glu Thr
                85                  90                  95

Ile Asp Ile Thr Met Pro Gly Ile Lys Gln Thr Val Gly Lys Arg His
            100                 105                 110
```

```
Pro Leu Glu Gln Thr Leu Glu Glu Met Lys Gln Ile Phe Ile Ser Met
        115                 120                 125

Gly Phe Thr Ile Glu Glu Gly Pro Glu Val Glu Lys Asp Tyr Tyr Asn
    130                 135                 140

Phe Glu Ala Leu Asn Ile Pro Lys Asn His Pro Ala Arg Gly Glu Gln
145                 150                 155                 160

Asp Thr Phe Tyr Ile Asn Asp Asn Val Val Leu Arg Thr Gln Thr Ser
                165                 170                 175

Pro Ile Gln Val Arg Thr Met Glu Lys Gln Lys Pro Pro Ile Lys Met
            180                 185                 190

Ile Ser Pro Gly Lys Val Tyr Arg Ser Asp Ser Val Asp Ala Thr His
        195                 200                 205

Ser Pro Ile Phe Tyr Gln Met Glu Gly Leu Val Val Asp Lys Gly Ile
    210                 215                 220

Thr Phe Ala Asn Leu Lys Gly Thr Leu Glu Leu Phe Ala Lys Lys Leu
225                 230                 235                 240

Phe Gly Asn Asp Ile Arg Thr Lys Phe Arg Pro His His Phe Pro Phe
                245                 250                 255

Thr Glu Pro Ser Ala Glu Met Asp Ala Ser Cys Phe Val Cys His Gly
            260                 265                 270

Lys Gly Cys Arg Val Cys Lys Gly Glu Gly Trp Ile Glu Leu Leu Gly
        275                 280                 285

Cys Gly Met Val His Pro Gln Val Leu Arg Asn Cys Gly Ile Asp Pro
    290                 295                 300

Glu Val Tyr Ser Gly Phe Gly Phe Gly Met Gly Val Asp Arg Met Val
305                 310                 315                 320

Met Leu Lys Tyr Gly Ile Asp Asp Ile Arg Asn Met Tyr Glu Ser Asp
                325                 330                 335

Met Arg Phe Leu Asn Gln Phe
            340
```

```
<210> SEQ ID NO 3
<211> LENGTH: 343
<212> TYPE: PRT
<213> ORGANISM: Artificial sequence
<220> FEATURE:
<223> OTHER INFORMATION: Synthetic

<400> SEQUENCE: 3

Met Lys Gly Glu Phe Lys Met Lys Glu Glu Leu Lys Gln Ile Lys Glu
1               5                   10                  15

Asn Ala Phe Asn Glu Leu Lys Asn Lys Lys Leu Asp Ile Glu Asp Ile
            20                  25                  30

Arg Val Lys Tyr Leu Gly Lys Lys Gly Glu Leu Thr Lys Ile Leu Arg
        35                  40                  45

Gly Met Lys Asp Leu Ser Lys Glu Glu Arg Pro Ala Ile Gly Lys Leu
    50                  55                  60

Ala Asn Glu Val Arg Ser Thr Leu Glu Asn Ala Ile Glu Glu Ala Ser
65                  70                  75                  80

Lys Lys Ile Lys Ser Ser Ala Ile Gln Ala Lys Leu Gln Asn Glu Thr
                85                  90                  95

Ile Asp Ile Thr Met Pro Gly Ile Lys Gln Thr Val Gly Lys Arg His
            100                 105                 110

Pro Leu Glu Gln Thr Leu Glu Glu Met Lys Gln Ile Phe Ile Ser Met
        115                 120                 125
```

```
Gly Phe Thr Ile Glu Glu Gly Pro Glu Val Glu Lys Asp Tyr Tyr Asn
    130                 135                 140

Phe Glu Ala Leu Asn Ile Pro Lys Asn His Pro Ala Arg Gly Glu Gln
145                 150                 155                 160

Asp Thr Phe Tyr Ile Asn Asp Asn Val Val Leu Arg Thr Gln Thr Ser
                165                 170                 175

Pro Ile Gln Val Arg Thr Met Glu Lys Gln Lys Pro Pro Ile Lys Met
            180                 185                 190

Ile Ser Pro Gly Lys Val Tyr Arg Ser Asp Ser Val Asp Ala Thr His
        195                 200                 205

Ser Pro Ile Phe Tyr Gln Met Glu Gly Leu Val Val Asp Lys Gly Ile
    210                 215                 220

Thr Phe Ala Asn Leu Lys Gly Thr Leu Glu Leu Phe Ala Lys Lys Leu
225                 230                 235                 240

Phe Gly Asn Asp Ile Arg Thr Lys Phe Arg Pro His His Phe Pro Phe
                245                 250                 255

Thr Glu Pro Ser Ala Glu Met Asp Ala Ser Cys Phe Val Cys His Gly
            260                 265                 270

Lys Gly Cys Arg Val Cys Lys Gly Glu Gly Trp Ile Glu Leu Leu Gly
        275                 280                 285

Cys Gly Met Val His Pro Gln Val Leu Arg Asn Cys Gly Ile Asp Pro
    290                 295                 300

Glu Val Tyr Ser Gly Phe Gly Phe Gly Met Gly Val Asp Arg Met Val
305                 310                 315                 320

Met Leu Lys Tyr Gly Ile Asp Asp Ile Arg Asn Met Tyr Glu Ser Asp
                325                 330                 335

Met Arg Phe Leu Asn Gln Phe
            340
```

```
<210> SEQ ID NO 4
<211> LENGTH: 1131
<212> TYPE: DNA
<213> ORGANISM: Artificial sequence
<220> FEATURE:
<223> OTHER INFORMATION: Synthetic

<400> SEQUENCE: 4

atggcttcgt accccctgcca tcaacacgcg tctgcgttcg accaggctgc gcgttctcgc     60

ggccatagca accgacgtac ggcgttgcgc cctcgccggc agcaagaagc cacggaagtc    120

cgcccggagc agaaaatgcc cacgctactg cgggtttata tagacggtcc ccacgggatg    180

gggaaaacca ccaccacgca actgctggtg gccctgggtt cgcgcgacga tatcgtctac    240

gtacccgagc cgatgactta ctggcgggtg ctgggggctt ccgagacaat cgcgaacatc    300

tacaccacac aacaccgcct cgaccagggt gagatatcgg ccggggacgc ggcggtggta    360

atgacaagcg cccagataac aatgggcatg ccttatgccg tgaccgacgc cgttctggct    420

cctcatatcg ggggggaggc tgggagctca catgccccgc ccccggccct caccctcatc    480

ttcgaccgcc atcccatcgc cgccctcctg tgctacccgg ccgcgcggta ccttatgggc    540

agcatgaccc cccaggccgt gctggcgttc gtggccctca tcccgccgac cttgcccggc    600

acaaacatcg tgttgggggc ccttccggag gacagacaca tcgaccgcct ggccaaacgc    660

cagcgccccg gtgagcggct tgacctggct atgctggccg cgattcgccg cgtttacggg    720

ctacttgcca atacggtgcg gtatctgcag tgcggcgggt cgtggcggga ggattgggga    780

cagctttcgg gagcggcctt gacgccccag ggtgccgagc cccagagcaa cgcgggccca    840
```

```
cgaccccata tcggggaaac gttatttacc ctgtttcggg cccccgagtt gctggccccc    900

aacggcgacc tgtacaacgt gtttgcctgg gccttggacg tcttggccaa acgcctccgt    960

cccatgcacg tctttatcct ggattacgac caatcgcccg ccggctgccg ggacgccctg   1020

ctgcaactta cctccgggat ggtccagacc catgtcacca ccccaggctc cataccgacg   1080

atctgcgacc tggcgcgcac gtttgcccgg gagatggggg aggctcactg a            1131


<210> SEQ ID NO 5
<211> LENGTH: 376
<212> TYPE: PRT
<213> ORGANISM: Artificial sequence
<220> FEATURE:
<223> OTHER INFORMATION: Synthetic

<400> SEQUENCE: 5

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Ala Ala Leu Thr Pro Gln Gly Ala
            260                 265                 270

Glu Pro Gln Ser Asn Ala Gly Pro Arg Pro His Ile Gly Glu Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
```

```
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala His
    370                 375


<210> SEQ ID NO 6
<211> LENGTH: 1599
<212> TYPE: DNA
<213> ORGANISM: Artificial sequence
<220> FEATURE:
<223> OTHER INFORMATION: Synthetic

<400> SEQUENCE: 6

ggccgcggcg ccaagcttag aaaaatataa ataagaagta gctttaagag aattaaatta      60

ttaagaaaag caaaggtgtt taaaaaataa atttttaaac acctttgctt ttcttaaatt     120

ataaataaga taaaaaagaa tcctgaataa aataaaaagg ggtgtctcaa aattttattt     180

tgagacgacc ccttttttatt ctatatgtcg atgctatagc tgagatcgtg gaattcttgt    240

tagctaccag attcacattt aagttgtttc tctaaaccac agattatcaa ttcaagtcca     300

aaaagaaatg ctggttctgc gccttgatga tcaaataact ctattgcttg tcttaacaat     360

ggaggcattg aatctgttgt tggtgtttct ctttcctctt ttgcaacttg atgttcttga     420

tcctccaata cgcaacctaa agtaaaatgt cctacagcac ttagtgcgta taaggcattt     480

tctaaactaa aaccctgttg acataagaat gctaattgat tttctaatgt ttcatattgt     540

ttttcagttg gtctagttcc taaatgtact ttagccccat ctctatgtga taatagagca     600

caacgaaaag atttagcgtt attcctaaga aaatcttgcc atgattcacc ttctaaagga     660

caaaagtgag tgtgatgtct atctaacatt tcaatagcta aggcgtcaag taaagctctc     720

ttattcttca catgccaata caacgtaggt tgttctactc caagtttctg agctaacttt     780

cttgtagtta gtccttctat tccaacttca tttagtaatt ccaatgcact attgataact     840

ttacttttat caagtctaga catcatttaa tatcctcctc ttcaatatat ttaagtcgac     900

tgatcggatc caatttatac gttttctcta acaacttaat tatacccact attattattt     960

ttatcaatat agagctccca tggcggccgg tcgatatcga tgtgtagtag cctgtgaaat    1020

aagtaaggaa aaaaaagaag taagtgttat atatgatgat tattttgtag atgtagatag    1080

gataatagaa tccatagaaa atataggtta tacagttata taaaaattac tttaaaatct    1140

atcattgata gggtaaaata taaatcgtat aaagttgtgt aatttttaag gaggtgtgtt    1200

acagacgtcc gcgagagacc ttaaatatat tgaagaggag gaaatacata tggtttcaag    1260

atatgttcca gatatgggag atttaatatg ggttgatttt gatccaacaa aaggatcaga    1320

acaagcagga catagaccag cagttgtttt atcaccattt atgtataata ataaaacagg    1380

aatgtgttta tgtgttccat gtacaacaca atcaaaagga tatccatttg aagttgtttt    1440

atcaggacaa gaaagagatg gagttgcatt agcagatcaa gttaaatcaa tagcatggag    1500

agcaagagga gcaacaaaaa aaggaacagt tgcaccagaa gaattacaat taataaaagc    1560

aaaaataaat gttttaatag gataatgtta ttaagctag                           1599
```

<210> SEQ ID NO 7
<211> LENGTH: 1327
<212> TYPE: DNA
<213> ORGANISM: Clostridium autoethanogenum

<400> SEQUENCE: 7

```
aatggcaggg cagataattg taatgatata gaatgtgatt tttatgtgga aggcagtaga      60
atcaaatgcc ttataagtgt attggcaatg aaagtgaaaa ataaaataat gggaatagtt     120
ataactttta gagaatgcaa atattatcac aaacttgtta aaaaagttat gggatatact     180
gcttcctata attttgacca tatagttact gctaattcta aaatgaaaga aataataaaa     240
tttgctaaaa aagcagcaag aagtgaatgc aatattttaa tagaagggga aagtggcact     300
ggaaaagaac tcttagctca atctattcac aattatagtg aaagatgtga aggccctttt     360
gtagctataa attgtagttc tatacctaga gaacttgtag aaagtgagct tttggttat      420
gaaaaaggag cttttacggg agctttaaag caaggaaagc ctggaaagtt tgaattagca     480
gatggaggaa ctattttttt ggatgaagta ggagagcttc ctcttgatat acagtcaaag     540
cttttaaggg ttcttgataa taataaaatt acaagagttg gaggaactta tgaaaaacag     600
ctaaatgtaa ggataatagg agctacaaac agggtgctca aggatgaaat taaaaagaaa     660
aatttcagaa gtgaccttta ttatagattg agtgtgatga atataaaaac tgtcccactt     720
agggaaagaa aagaagatat agagctttta attaaatatt ttatggaaga attgaattct     780
aaaagtttgt gtaagaagaa agtagtggaa aaagcataca tagaaaagat taaagcttat     840
gattggcctg gaaatgttag agaacttaga aatgtaatag agagggatta ctatttaagt     900
gaggataaga tggccccttt ggattattta gaaaaagaag tttatgaaaa aaatgtctcc     960
tctgatccag taaatattag tgtgcttcca atggatgttt tagaaaaaga aaacattgaa    1020
aatgcactta aaaagtgtaa gggaaatata ttaaaagctg caaaatcttt aaatatcagt    1080
agatctacca tgtatagaaa aatgaaaaag tatggaataa aaagtgtgtc aaaatgacca    1140
gaaaagagta agattctcaa aataggacac taagtatgtg tcataatggc acatagtgat    1200
tttaaatgtc tttttaacag gtttcttgtt tttggtatgg cttttgctta taaaatatag    1260
tgaatatatt aacaggtata tgtaaatttt aatattgcca tactattata aaaaaggaga    1320
gataatt                                                              1327
```

<210> SEQ ID NO 8
<211> LENGTH: 211
<212> TYPE: DNA
<213> ORGANISM: Clostridium autoethanogenum

<400> SEQUENCE: 8

```
aaagtactca tagaattgat taaaaaatga attcagcaaa ttatgtggtt gaattcattt      60
tttttgttgt aaattaacat ttatataaaa ataatggtat acttagatgt aattgaaagt     120
tttcagttat attgaggagg ccaaaaatga gctttaagaa aaatgtatac gatacaatga     180
gggaactaat atctgtgcca agcatatctg g                                   211
```

<210> SEQ ID NO 9
<211> LENGTH: 1074
<212> TYPE: DNA
<213> ORGANISM: Clostridium autoethanogenum

<400> SEQUENCE: 9

```
atgaaagctg tattgtggta tgataaaaaa gatgtaagag tagaggaaat tgaggaacct      60
```

```
aaggtaaaag aaaatgctgt aaaaattaaa gtgaaatggt gtggtatatg tggttctgac    120

ttgcatgagt atttaggagg acctatattt attccagtag gtacgccaca tcctttaagc    180

aagagtactg caccagtagt tttaggacat gagttttcag gagaagtagt agaaatagga    240

agcaaggtta caaaatttaa agcaggagat agagttattg tagaacctat agttgcctgt    300

ggaaagtgtc ctgcttgtct tgaaggaaaa tataatttat gtgaagcttt gggatttcat    360

ggactttgtg gaagcggcgg cggatttgct gaatacacag tatttcctga agattttgtc    420

cataagatac cagatactat ggactatgag caggctgcac ttgttgagcc tatggcagtt    480

gcccttcatt ctctaagagt tggaaacttt actacaggaa atactgcttt ggttttaggt    540

gcaggaccta taggacttgc aactattcag tgtttaaagg catcaggggc aagaattgta    600

attgtatttc agagaaaatc tgtaagacag gaatatgcta agaaatttgg agcagatgta    660

gttttagatc caaatgaggt agatgtaatt gaagaaatta aaaaacttac aggcggcgta    720

ggcgtggata catcttttga aacaacaggt gcaaatgtag ggattaatac ggcaattcaa    780

gctttaaaat atgaaggtac tgcggtaata accagcgtat gggagaaaaa tgcagaaatc    840

aatccaaatg atcttgtatt tacagaaaag aaggtagttg gtactcttgc ctacagacat    900

gaatttcctt ctacaatagc acttatgaat gatggaagaa taaagacaga cggatatatt    960

acaaagagaa tagcacttga ggacattgta aaagaaggat ttgaaacact tacaggacct   1020

gaaaagaaaa aacatgtaaa aataattgta actcctgaca aatccttatt gtaa         1074
```

<210> SEQ ID NO 10
<211> LENGTH: 3364
<212> TYPE: DNA
<213> ORGANISM: Clostridium autoethanogenum

<400> SEQUENCE: 10

```
aatggcaggg cagataattg taatgatata gaatgtgatt tttatgtgga aggcagtaga     60

atcaaatgcc ttataagtgt attggcaatg aaagtgaaaa ataaaataat gggaatagtt    120

ataactttta gagaatgcaa atattatcac aaacttgtta aaaaagttat gggatatact    180

gcttcctata attttgacca tatagttact gctaattcta aaatgaaaga aataataaaa    240

tttgctaaaa aagcagcaag aagtgaatgc aatattttaa tagaagggga aagtggcact    300

ggaaaagaac tcttagctca atctattcac aattatagtg aaagatgtga aggccctttt    360

gtagctataa attgtagttc tatacctaga gaacttgtag aaagtgagct tttggttat     420

gaaaaaggag cttttacggg agctttaaag caaggaaagc ctggaaagtt tgaattagca    480

gatggaggaa ctattttttt ggatgaagta ggagagcttc ctcttgatat acagtcaaag    540

cttttaaggg ttcttgataa taataaaatt acaagagttg gaggaactta tgaaaaacag    600

ctaaatgtaa ggataatagg agctacaaac agggtgctca aggatgaaat taaaaagaaa    660

aatttcagaa gtgaccttta ttatagattg agtgtgatga atataaaaac tgtcccactt    720

agggaaagaa aagaagatat agagctttta attaaatatt ttatggaaga attgaattct    780

aaaagtttgt gtaagaagaa agtagtggaa aaagcataca tagaaaagat taaagcttat    840

gattggcctg gaaatgttag agaacttaga aatgtaatag agagggatta ctatttaagt    900

gaggataaga tggccccttt ggattattta gaaaaagaag tttatgaaaa aaatgtctcc    960

tctgatccag taaatattag tgtgcttcca atggatgttt tagaaaaaga aaacattgaa   1020

aatgcactta aaaagtgtaa gggaaatata ttaaaagctg caaaatcttt aaatatcagt   1080

agatctacca tgtatagaaa aatgaaaaag tatggaataa aaagtgtgtc aaaatgacca   1140
```

```
gaaaagagta agattctcaa aataggacac taagtatgtg tcataatggc acatagtgat   1200
tttaaatgtc tttttaacag gtttcttgtt tttggtatgg cttttgctta taaaatatag   1260
tgaatatatt aacaggtata tgtaaatttt aatattgcca tactattata aaaaaggaga   1320
gataattatg aaagctgtat tgtggtatga taaaaaagat gtaagagtag aggaaattga   1380
ggaacctaag gtaaaagaaa atgctgtaaa aattaaagtg aaatggtgtg gtatatgtgg   1440
ttctgacttg catgagtatt taggaggacc tatatttatt ccagtaggta cgccacatcc   1500
tttaagcaag agtactgcac cagtagtttt aggacatgag ttttcaggag aagtagtaga   1560
aataggaagc aaggttacaa aatttaaagc aggagataga gttattgtag aacctatagt   1620
tgcctgtgga aagtgtcctg cttgtcttga aggaaaatat aatttatgtg aagctttggg   1680
atttcatgga ctttgtggaa gcggcggcgg atttgctgaa tacacagtat ttcctgaaga   1740
ttttgtccat aagataccag atactatgga ctatgagcag gctgcacttg ttgagcctat   1800
ggcagttgcc cttcattctc taagagttgg aaactttact acaggaaata ctgctttggt   1860
tttaggtgca ggacctatag gacttgcaac tattcagtgt ttaaaggcat caggggcaag   1920
aattgtaatt gtatttcaga gaaaatctgt aagacaggaa tatgctaaga aatttggagc   1980
agatgtagtt ttagatccaa atgaggtaga tgtaattgaa gaaattaaaa aacttacagg   2040
cggcgtaggc gtggatacat cttttgaaac aacaggtgca aatgtaggga ttaatacggc   2100
aattcaagct ttaaaatatg aaggtactgc ggtaataacc agcgtatggg agaaaaatgc   2160
agaaatcaat ccaaatgatc ttgtatttac agaaaagaag gtagttggta ctcttgccta   2220
cagacatgaa tttccttcta caatagcact tatgaatgat ggaagaataa agacagacgg   2280
atatattaca aagagaatag cacttgagga cattgtaaaa gaaggatttg aaacacttac   2340
aggacctgaa aagaaaaaac atgtaaaaat aattgtaact cctgacaaat ccttattgta   2400
aaaagtactc atagaattga ttaaaaaatg aattcagcaa attatgtggt tgaattcatt   2460
ttttttgttg taaattaaca tttatataaa aataatggta tacttagatg taattgaaag   2520
ttttcagtta tattgaggag gccaaaaatg agctttaaga aaaatgtata cgatacaatg   2580
agggaactaa tatctgtgcc aagcatatct ggtacaaaag aagagtgtgc ggcagcagaa   2640
aaaatatatg aaaaaatttt ggaaatacct tattttaagg acaatcctga aaatctagga   2700
atagagcaaa ttgaagatga tcctttagga agaagctttg tatgggcagt agtaaatgga   2760
aatgaaaatt caccaaattc gtttatactt tcaggtcatt tggatgtagt tggagtagaa   2820
gaatttggac atttaaaatc tatggctttt gatgtagatg aatgtactaa aagaatctca   2880
gaattgaatt tagatgaaga tgctatggag gattttaaat caggagattg gatatttgga   2940
aggggaactg cagacatgaa gtttggagtg gccctcaata tggaactttt aagagaattc   3000
agtaaagaga gaaactttaa gggaaactta ttacttttag tagttcctgg tgaagagagt   3060
aattccgaag gaatgattgc tgcagctcca tttcttctta aattaaagga agagaggaag   3120
tacaattact gtggtatgat aatatcagag ccaagtatac ctgaaagagg agaaaaagaa   3180
ggcaagagat tatatatagg tagtgtaggt aaaattatgc ctttattttt ttgtgtggga   3240
aaagaaactc atgtagggga atctttaaga ggattgaatc caaatttgct agtttcagag   3300
ataaacaaat taatggaatg taatccagat ctctcagata gcgtttatga tactgtgact   3360
ccac                                                                3364
```

<210> SEQ ID NO 11

<211> LENGTH: 5563
<212> TYPE: DNA
<213> ORGANISM: Clostridium autoethanogenum

<400> SEQUENCE: 11

```
aatggcaggg cagataattg taatgatata gaatgtgatt tttatgtgga aggcagtaga     60

atcaaatgcc ttataagtgt attggcaatg aaagtgaaaa ataaaataat gggaatagtt    120

ataactttta gagaatgcaa atattatcac aaacttgtta aaaaagttat gggatatact    180

gcttcctata attttgacca tatagttact gctaattcta aaatgaaaga aataataaaa    240

tttgctaaaa aagcagcaag aagtgaatgc aatattttaa tagaagggga aagtggcact    300

ggaaaagaac tcttagctca atctattcac aattatagtg aaagatgtga aggccctttt    360

gtagctataa attgtagttc tatacctaga gaacttgtag aaagtgagct tttggttat     420

gaaaaaggag cttttacggg agctttaaag caaggaaagc ctggaaagtt tgaattagca    480

gatggaggaa ctattttttt ggatgaagta ggagagcttc ctcttgatat acagtcaaag    540

cttttaaggg ttcttgataa taataaaatt acaagagttg gaggaactta tgaaaaacag    600

ctaaatgtaa ggataatagg agctacaaac agggtgctca aggatgaaat taaaaagaaa    660

aatttcagaa gtgaccttta ttatagattg agtgtgatga atataaaaac tgtcccactt    720

agggaaagaa aagaagatat agagctttta attaaatatt ttatggaaga attgaattct    780

aaaagtttgt gtaagaagaa agtagtggaa aaagcataca tagaaaagat taaagcttat    840

gattggcctg gaaatgttag agaacttaga aatgtaatag agagggatta ctatttaagt    900

gaggataaga tggccccttt ggattattta gaaaaagaag tttatgaaaa aaatgtctcc    960

tctgatccag taaatattag tgtgcttcca atggatgttt tagaaaaaga aaacattgaa   1020

aatgcactta aaaagtgtaa gggaaatata ttaaaagctg caaaatcttt aaatatcagt   1080

agatctacca tgtatagaaa aatgaaaaag tatggaataa aaagtgtgtc aaaatgacca   1140

gaaaagagta agattctcaa aataggacac taagtatgtg tcataatggc acatagtgat   1200

tttaaatgtc tttttaacag gtttcttgtt tttggtatgg cttttgctta taaaatatag   1260

tgaatatatt aacaggtata tgtaaatttt aatattgcca tactattata aaaaaggaga   1320

gataattatg aaagctgtat tgtggtatga taaaaaagat gtaagagtag aggaaattga   1380

ggaacctaag gtaaaagaaa atgctgtaaa aattaaagtg aaatggtgtg gtatatgtgg   1440

ttctgacttg catgagtatt taggaggacc tatatttatt ccagtaggta cgccacatcc   1500

tttaagcaag agtactgcac cagtagtttt aggacatgag ttttcaggag aagtagtaga   1560

aataggaagc aaggttacaa aatttaaagc aggagataga gttattgtag aacctatagt   1620

tgcctgtgga aagtgtcctg cttgtcttga aggaaaatat aatttatgtg aagctttggg   1680

atttcatgga ctttgtggaa gcggcggcgg atttgctgaa tacacagtat ttcctgaaga   1740

ttttgtccat aagataccag atactatgga ctatgagcag gctgcacttg ttgagcctat   1800

ggcagttgcc cttcattctc taagagttgg aaactttact acaggaaata ctgctttggt   1860

tttaggtgca ggacctatag gacttgcaac tattcagtgt ttaaaggcat caggggcaag   1920

aattgtaatt gtatttcaga gaaaatctgt aagacaggaa tatgctaaga aatttggagc   1980

agatgtagtt ttagatccaa atgaggtaga tgtaattgaa gaaattaaaa aacttacagg   2040

cggcgtaggc gtggatacat cttttgaaac aacaggtgca aatgtaggga ttaatacggc   2100

aattcaagct ttaaaatatg aaggtactgc ggtaataacc agcgtatggg agaaaaatgc   2160

agaaatcaat ccaaatgatc ttgtatttac agaaaagaag gtagttggta ctcttgccta   2220
```

```
cagacatgaa tttccttcta caatagcact tatgaatgat ggaagaataa agacagacgg   2280
atatattaca aagagaatag cacttgagga cattgtaaaa gaaggatttg aaacacttac   2340
aggacctgaa aagaaaaaac atgtaaaaat aattgtaact cctgacaaat ccttattgta   2400
aggatcctag tcagggcaag ttgaaaaatt cacaaaaatg tggtataata tctttgttca   2460
ttagagcgat aaacttgaat ttgagaggga acttagatgg tatttgaaaa aattgataaa   2520
aatagttgga acagaaaaga gtattttgac cactactttg caagtgtacc ttgtacctac   2580
agcatgaccg ttaaagtgga tatcacacaa ataaaggaaa agggaatgaa actatatcct   2640
gcaatgcttt attatattgc aatgattgta aaccgccatt cagagtttag gacggcaatc   2700
aatcaagatg gtgaattggg gatatatgat gagatgatac caagctatac aatatttcac   2760
aatgatactg aaacattttc cagcctttgg actgagtgta agtctgactt taaatcattt   2820
ttagcagatt atgaaagtga tacgcaacgg tatggaaaca atcatagaat ggaaggaaag   2880
ccaaatgctc cggaaaacat ttttaatgta tctatgatac cgtggtcaac cttcgatggc   2940
tttaatctga atttgcagaa aggatatgat tatttgattc ctatttttac tatggggaaa   3000
tattataaag aagataacaa aattatactt cctttggcaa ttcaagttca tcacgcagta   3060
tgtgacggat ttcacatttg ccgttttgta aacgaattgc aggaattgat aaatagttaa   3120
gagctcagga ggatagtata tggcttcgta cccctgccat caacacgcgt ctgcgttcga   3180
ccaggctgcg cgttctcgcg gccatagcaa ccgacgtacg gcgttgcgcc ctcgccggca   3240
gcaagaagcc acggaagtcc gcccggagca gaaaatgccc acgctactgc gggtttatat   3300
agacggtccc cacgggatgg ggaaaaccac caccacgcaa ctgctggtgg ccctgggttc   3360
gcgcgacgat atcgtctacg tacccgagcc gatgacttac tggcgggtgc tgggggcttc   3420
cgagacaatc gcgaacatct acaccacaca acaccgcctc gaccagggtg agatatcggc   3480
cggggacgcg gcggtggtaa tgacaagcgc ccagataaca atgggcatgc cttatgccgt   3540
gaccgacgcc gttctggctc ctcatatcgg gggggaggct gggagttcac atgccccgcc   3600
cccggccctc accctcatct tcgaccgcca tcccatcgcc gccctcctgt gctacccggc   3660
cgcgcggtac cttatgggca gcatgacccc ccaggccgtg ctggcgttcg tggccctcat   3720
cccgccgacc ttgcccggca caaacatcgt gttgggggcc cttccggagg acagacacat   3780
cgaccgcctg gccaaacgcc agcgccccgg tgagcggctt gacctggcta tgctggccgc   3840
gattcgccgc gtttacgggc tacttgccaa tacggtgcgg tatctgcagt gcggcgggtc   3900
gtggcgggag gattggggac agctttcggg agcggccttg acgccccagg gtgccgagcc   3960
ccagagcaac gcgggcccac gaccccatat cggggaaacg ttatttaccc tgtttcgggc   4020
ccccgagttg ctggccccca acggcgacct gtacaacgtg tttgcctggg ccttggacgt   4080
cttggccaaa cgcctccgtc ccatgcacgt ctttatcctg gattacgacc aatcgcccgc   4140
cggctgccgg gacgccctgc tgcaacttac ctccgggatg gtccagaccc atgtcaccac   4200
cccaggctcc ataccgacga tctgcgacct ggcgcgcacg tttgcccggg agatggggga   4260
ggctcactga taaatcgatt taaaaagtgt aagggaaata tattaaaagc tgcaaaatct   4320
ttaaatatca gtagatctac catgtataga aaaatgaaaa agtatggaat aaaaagtgtg   4380
tcaaaatgac cagaaaagag taagattctc aaaataggac actaagtatg tgtcataatg   4440
gcacatagtg attttaaatg tctttttaac aggtttcttg tttttggtat ggcttttgct   4500
tataaaatat agtgaatata ttaacaggta tatgtaaatt ttaatattgc catactatta   4560
```

```
taaaaaagga gagataattg cggccgctag tagcgctagc aaagtactca tagaattgat   4620

taaaaaatga attcagcaaa ttatgtggtt gaattcattt tttttgttgt aaattaacat   4680

ttatataaaa ataatggtat acttagatgt aattgaaagt tttcagttat attgaggagg   4740

ccaaaaatga gctttaagaa aaatgtatac gatacaatga gggaactaat atctgtgcca   4800

agcatatctg gtacaaaaga agagtgtgcg gcagcagaaa aaatatatga aaaaattttg   4860

gaaatacctt attttaagga caatcctgaa aatctaggaa tagagcaaat tgaagatgat   4920

cctttaggaa gaagctttgt atgggcagta gtaaatggaa atgaaaattc accaaattcg   4980

tttatacttt caggtcattt ggatgtagtt ggagtagaag aatttggaca tttaaaatct   5040

atggcttttg atgtagatga atgtactaaa agaatctcag aattgaattt agatgaagat   5100

gctatggagg attttaaatc aggagattgg atatttggaa ggggaactgc agacatgaag   5160

tttggagtgg ccctcaatat ggaacttttta agagaattca gtaaagagag aaactttaag   5220

ggaaacttat tacttttagt agttcctggt gaagagagta attccgaagg aatgattgct   5280

gcagctccat ttcttcttaa attaaaggaa gagaggaagt acaattactg tggtatgata   5340

atatcagagc caagtatacc tgaaagagga gaaaaagaag gcaagagatt atatataggt   5400

agtgtaggta aaattatgcc tttatttttt tgtgtgggaa aagaaactca tgtaggggaa   5460

tctttaagag gattgaatcc aaatttgcta gtttcagaga taaacaaatt aatggaatgt   5520

aatccagatc tctcagatag cgtttatgat actgtgactc cac                    5563
```

<210> SEQ ID NO 12
<211> LENGTH: 2310
<212> TYPE: DNA
<213> ORGANISM: Clostridium autoethanogenum

<400> SEQUENCE: 12

```
aatggcaggg cagataattg taatgatata gaatgtgatt tttatgtgga aggcagtaga     60

atcaaatgcc ttataagtgt attggcaatg aaagtgaaaa ataaaataat gggaatagtt    120

ataactttta gagaatgcaa atattatcac aaacttgtta aaaaagttat gggatatact    180

gcttcctata attttgacca tatagttact gctaattcta aaatgaaaga aataataaaa    240

tttgctaaaa aagcagcaag aagtgaatgc aatattttaa tagaagggga aagtggcact    300

ggaaaagaac tcttagctca atctattcac aattatagtg aaagatgtga aggccctttt    360

gtagctataa attgtagttc tatacctaga gaacttgtag aaagtgagct ttttggttat    420

gaaaaaggag cttttacggg agctttaaag caaggaaagc ctggaaagtt tgaattagca    480

gatggaggaa ctattttttt ggatgaagta ggagagcttc ctcttgatat acagtcaaag    540

cttttaaggg ttcttgataa taataaaatt acaagagttg gaggaactta tgaaaaacag    600

ctaaatgtaa ggataatagg agctacaaac agggtgctca aggatgaaat taaaaagaaa    660

aatttcagaa gtgaccttta ttatagattg agtgtgatga atataaaaac tgtcccactt    720

agggaaagaa aagaagatat agagctttta attaaatatt ttatggaaga attgaattct    780

aaaagtttgt gtaagaagaa agtagtggaa aaagcataca tagaaaagat taaagcttat    840

gattggcctg gaaatgttag agaacttaga aatgtaatag agagggatta ctatttaagt    900

gaggataaga tggccccttt ggattattta gaaaaagaag tttatgaaaa aaatgtctcc    960

tctgatccag taaatattag tgtgcttcca atggatgttt tagaaaaaga aaacattgaa   1020

aatgcactta aaaagtgtaa gggaaatata ttaaaagctg caaaatcttt aaatatcagt   1080

agatctacca tgtatagaaa atgaaaaagt atggaataaa aagtgtgtca aaatgaccag   1140
```

```
aaaagagtaa gattctcaaa ataggacact aagtatgtgt cataatggca catagtgatt   1200

ttaaatgtct ttttaacagg tttcttgttt ttggtatggc ttttgcttat aaaatatagt   1260

gaatatatta acaggtatat gtaaatttta atattgccat actattataa aaaaggagag   1320

ataattgcgg ccgctagtag cgctagcaaa gtactcatag aattgattaa aaaatgaatt   1380

cagcaaatta tgtggttgaa ttcatttttt ttgttgtaaa ttaacattta tataaaaata   1440

atggtatact tagatgtaat tgaaagtttt cagttatatt gaggaggcca aaaatgagct   1500

ttaagaaaaa tgtatacgat acaatgaggg aactaatatc tgtgccaagc atatctggta   1560

caaaagaaga gtgtgcggca gcagaaaaaa tatatgaaaa aattttggaa ataccttatt   1620

ttaaggacaa tcctgaaaat ctaggaatag agcaaattga agatgatcct ttaggaagaa   1680

gctttgtatg ggcagtagta aatggaaatg aaaattcacc aaattcgttt atactttcag   1740

gtcatttgga tgtagttgga gtagaagaat ttggacattt aaaatctatg gcttttgatg   1800

tagatgaatg tactaaaaga atctcagaat tgaatttaga tgaagatgct atggaggatt   1860

ttaaatcagg agattggata tttggaaggg gaactgcaga catgaagttt ggagtggccc   1920

tcaatatgga acttttaaga gaattcagta aagagagaaa ctttaaggga aacttattac   1980

ttttagtagt tcctggtgaa gagagtaatt ccgaaggaat gattgctgca gctccatttc   2040

ttcttaaatt aaaggaagag aggaagtaca attactgtgg tatgataata tcagagccaa   2100

gtatacctga aagaggagaa aaagaaggca agagattata tataggtagt gtaggtaaaa   2160

ttatgccttt atttttttgt gtgggaaaag aaactcatgt aggggaatct ttaagaggat   2220

tgaatccaaa tttgctagtt tcagagataa acaaattaat ggaatgtaat ccagatctct   2280

cagatagcgt ttatgatact gtgactccac                                    2310
```

```
<210> SEQ ID NO 13
<211> LENGTH: 1056
<212> TYPE: DNA
<213> ORGANISM: Clostridium autoethanogenum

<400> SEQUENCE: 13

atgaaaggtt ttgcaatgtt aggtattaac aaattaggat ggattgaaaa gaaaaaccca     60

gtgccaggtc cttatgatgc gattgtacat cctctagctg tatccccatg tacatcagat    120

atacatacgg tttttgaagg agcacttggt aatagggaaa atatgatttt aggccatgaa    180

gctgtaggtg aaatagccga agttggcagc gaagttaaag attttaaagt tggcgataga    240

gttatcgtac catgcacaac acctgactgg agatctttag aagtccaagc tggttttcag    300

cagcattcaa acggtatgct tgcaggatgg aagttttcca attttaaaga tggtgtattt    360

gcagattact ttcatgtaaa cgatgcagat atgaatcttg ccatactccc agatgaaata    420

cctttagaaa gtgcagttat gatgacagac atgatgacta ctggttttca tggagcagaa    480

cttgcagaca taaaaatggg ctccagcgtt gtagtaattg gtataggagc tgttggatta    540

atgggaatag ccggttccaa acttcgagga gcaggcagaa ttatcggtgt tggaagcaga    600

cctgtttgtg ttgaaacagc taaattttat ggagcaactg atattgtaaa ttataaaaat    660

ggtgatatag ttgaacaaat catggactta actcatggta aaggtgtaga ccgtgtaatc    720

atggcaggcg gtggtgctga aacactagca caagcagtaa ctatggttaa acctggcggc    780

gtaatttcta acatcaacta ccatggaagc ggtgatactt taccaatacc tcgtgttcaa    840

tggggctgcg gcatggctca caaaactata agaggaggat tatgccccgg cggacgtctt    900
```

-continued

```
agaatggaaa tgctaagaga tcttgttcta tataaacgtg ttgatttgag taaacttgtt    960

actcatgtat ttgatggtgc agaaaatatt gaaaaggccc ttttgcttat gaaaaataag   1020

ccaaaagatt taattaaatc agtagttaca ttctaa                             1056
```

METHOD OF PRODUCING A RECOMBINANT MICROORGANISM

CROSS REFERENCE TO RELATED APPLICATIONS

This application claims the benefit of U.S. Provisional Patent Application 61/932,737 filed Jan. 28, 2014, the entirety of which is incorporated herein by reference.

SEQUENCE LISTING

This application includes a nucleotide/amino acid sequence listing submitted concurrently herewith and identified as follows: 35,226 byte ASCII (text) file named "LT099US1_ST25.txt" created on Jan. 28, 2015, the entirety of which is incorporated herein by reference.

BACKGROUND OF THE INVENTION

Sophisticated and varied genetic tools exist for manipulating the genomes of established model microorganisms, such as *Escherichia coli* and *Saccharomyces cerevisiae*. However, for many other microorganisms of biotechnological interest, only exceedingly basic genetic tools are available, which makes it difficult to evaluate and optimize such microorganisms for medical, chemical, or industrial applications.

For example, genetic tools are lacking for the genus *Clostridium*, which includes Gram-positive, spore-forming, anaerobic bacteria. Species such as *Clostridium difficile, Clostridium botulinum*, and *Clostridium perfringens* are pathogenic and/or have important medical applications. Additionally, species such as *Clostridium acetobutylicum, Clostridium beijerinckii, Clostridium celluloyticum, Clostridium ljungdahlii, Clostridium butyricum*, and *Clostridium autoethanogenum* ferment sugars, biomass, and gases to produce various biofuels and biochemical products.

Existing genetic tools for *Clostridium*, such as ClosTron (Heap, *J Microbiol Meth,* 70:452-464, 2007), allele coupled exchange (ACE) (Heap, *Nucleic Acids Res,* 40: e59, 2012), and counter selection markers (Ng, *PLoS ONE,* 8: e56051, 2013; Al-Hinai, *Appl Environ Microbiol,* 78: 8112-8121, 2012; Cartman, *Appl Environ Microbiol,* 78: 4683-4690, 2012; WO 2010/084349), allow only rudimentary genetic manipulation compared to genetic tools for model microorganisms like *Escherichia coli* and *Saccharomyces cerevisiae*. Moreover, the genetic tools that do exist often require multiple steps to achieve the desired modification, cumbersome mutant screening processes, and fickle transformation steps. Accordingly, there is a strong need for robust genetic tools and methods for manipulating the genomes of non-model microorganisms, such as *Clostridium* bacteria.

SUMMARY OF THE INVENTION

The invention provides genetic tools to insert, replace, delete, or otherwise manipulate a nucleic acid sequence in a microorganism to produce a recombinant microorganism. In particular, invention provides a method of producing a recombinant microorganism, comprising:

(a) providing a microorganism comprising a genetic element comprising a target nucleic acid T1, a target nucleic acid T2, and a target nucleic acid T3, (b) providing a DNA construct comprising a left homology arm LHA1 homologous to T1, a right homology arm RHA1 homologous to T2, and a right homology arm RHA2 homologous to T3, wherein RHA2 is located between LHA1 and RHA1, (c) allowing the genetic element of (a) to undergo homologous recombination with the DNA construct of (b), whereby T1 aligns with LHA1 and T2 aligns with RHA1 to insert the portion of the DNA construct between LHA1 and RHA1, including RHA2, into the genetic element between T1 and T2, and (d) allowing the genetic element of (c) to undergo self-homologous recombination, whereby T3 aligns with RHA2 to remove the portion of the genetic element between T3 and RHA2.

In one embodiment, the genetic element of (a) comprises 5'-T3-T1-T2-3'; the DNA construct of (b) comprises 5'-LHA1-RHA2-RHA1-3'; a microorganism comprising a genetic element comprising 5'-T3-T1-RHA2-T2-3' is formed in (c); and a microorganism comprising a genetic element comprising 5'-T3-T2-3' is formed in (d), such that T1 is deleted from the genetic element.

In one embodiment, the genetic element of (a) comprises 5'-T3-T1-T2-3'; the DNA construct of (b) comprises 5'-LHA1-RHA2-IS1-RHA1-3' wherein IS1 is an insertion nucleic acid; a microorganism comprising a genetic element comprising 5'-T3-T1-RHA2-IS1-T2-3' is formed in (c); and a microorganism comprising a genetic element comprising 5'-T3-IS1-T2-3' is formed in (d), such that T1 is replaced by IS1 in the genetic element.

In one embodiment, the genetic element of (a) comprises 5'-$T1_{T3}$-T4-T2-3' wherein T1 encompasses T3 and T4 is a target nucleic acid; the DNA construct of (b) comprises 5'-$LHA1_{RHA2}$-RHA2-RHA1-3' wherein LHA1 encompasses RHA2; a microorganism comprising a genetic element comprising 5'-$T1_{T3}$-RHA2-T2-3' is formed in (c); and a microorganism comprising a genetic element comprising 5'-$T1_{T3}$-T2-3' is formed in (d), such that T4 is deleted from the genetic element.

In one embodiment, the genetic element of (a) comprises 5'-$T1_{T3}$-T2-3' wherein T1 encompasses T3; the DNA construct of (b) comprises 5'-$LHA1_{RHA2}$-RHA2-IS1-RHA1-3' wherein LHA1 encompasses RHA2 and IS1 is an insertion nucleic acid; a microorganism comprising a genetic element comprising 5'-$T1_{T3}$-RHA2-IS1-T2-3' is formed in (c); and a microorganism comprising a genetic element comprising 5'-$T1_{T3}$-IS1-T2-3' is formed in (d), such that IS1 is inserted in the genetic element.

In one embodiment, the genetic element of (a) comprises 5'-$T1_{T3}$-T4-T2-3' wherein T1 encompasses T3 and T4 is a target nucleic acid; the DNA construct of (b) comprises 5'-$LHA1_{RHA2}$-RHA2-IS1-RHA1-3' wherein LHA1 encompasses RHA2 and IS1 is an insertion nucleic acid; a microorganism comprising a genetic element comprising 5'-$T1_{T3}$-RHA2-IS1-T2-3' is formed in (c); and a microorganism comprising a genetic element comprising 5'-$T1_{T3}$-IS1-T2-3' is formed in (d), such that T4 is replaced by IS1 in the genetic element.

In one embodiment, the DNA construct of (b) further comprises a counter selection marker CS1 upstream of LHA1 and a positive selection marker PS1 and a counter selection marker CS2 between LHA1 and RHA2. In a further embodiment, (c) is followed by a step of selecting for expression of PS1 and against expression of CS1 and (d) is followed by a step of selecting against expression of CS2. CS1 and CS2 may be independently selected from the group consisting of pheS*, upp, sacB, tetAR, thyA, ccdB, lacY, rpsL, codA, pyrE, HSTK (thiK), gatA-1, and mazF; and PS1 may be selected from the group consisting of catP, tetA(C), tetM, aad9, aadA, aadA2, and ermB.

In one embodiment, the DNA construct of (b) further comprises a counter selection marker CS1 upstream of LHA1 and a positive selection marker PS1 between LHA1 and RHA2. In a further embodiment, (c) is followed by a step of selecting for expression of PS1 and against expression of CS1. CS1 may be selected from the group consisting of pheS*, upp, sacB, tetAR, thyA, ccdB, lacY, rpsL, codA, pyrE, HSTK (thiK), gatA-1, and mazF; and PS1 may be selected from the group consisting of catP, tetA(C), tetM, aad9, aadA, aadA2, and ermB.

In one embodiment, LHA1 is longer than RHA2. In particular, LHA1 may be equal to or greater than about 1000 base pairs in length and RHA2 may be equal to or less than about 300 base pairs in length.

In one embodiment, LHA1 and RHA1 are each longer than RHA2. In particular, LHA1 and RHA1 may each be equal to or greater than about 1000 base pairs in length and RHA2 may be equal to or less than about 300 base pairs in length.

In one embodiment, the microorganism is a bacterium, archea, virus, or fungus. For example, the microorganism may belong to genus *Clostridium, Acetobacterium, Moorella, Butyribacterium, Blautia, Oxobacter, Thermoanaerobacter, Escherichia, Klebsiella, Zymomonas, Citrobacter, Enterobacter, Salmonella, Serratia, Lactobacillus, Lactococcus, Enterococcus, Pediococcus, Streptococcus, Saccharomyces, Pichia, Candida Hansenula, Yarrowia, Rhodotorula, Rhizopus, Trichosporon, Lipomyces, Aspergillus, trichoderma, Exophila, Mucor, Cladosporium, Phanerochaete, Cladiophilalophora, Paecilomyces, Scedosporium, Ophistoma, Bacillus, Oligotropha, Pseudomonas, Carbophilus, Hydrogenophaga, Mycobacterium, Zavarzinia, Cupravidus, Senechocystis, Chloroflexus, Methylomonas, Methylobacter, Methylococcus, Methylomicrobium, Methylosphera, Methylocaldum, Methylocystis, Methylosinus, Methanobacterium, Methanococcus, Methanogenium, Methanosarcina, Methanoshera, Methanothermobacter, Methanotrix, Corynebacterium, Acinetobacter, Actinomyces, Bacteroides, Burkholderia, Brevibacterium, Pyrococcus, Geobacter, Geobacillus, Paenibacillus, Mycobacterium, Rhodopseudomonas, Thermatoga, Thermoanaerobacter, Streptomyces, Rhodobacter, Rhodococcus, Peptococcus, Bifidobacterium, Propionibacterium, Fusobacterium, Campylobacter, Veillonella, Aquincola, Arthrobacter, Moraxella*, or *Psychrobacter.*

DETAILED DESCRIPTION OF THE INVENTION

Figure 1:
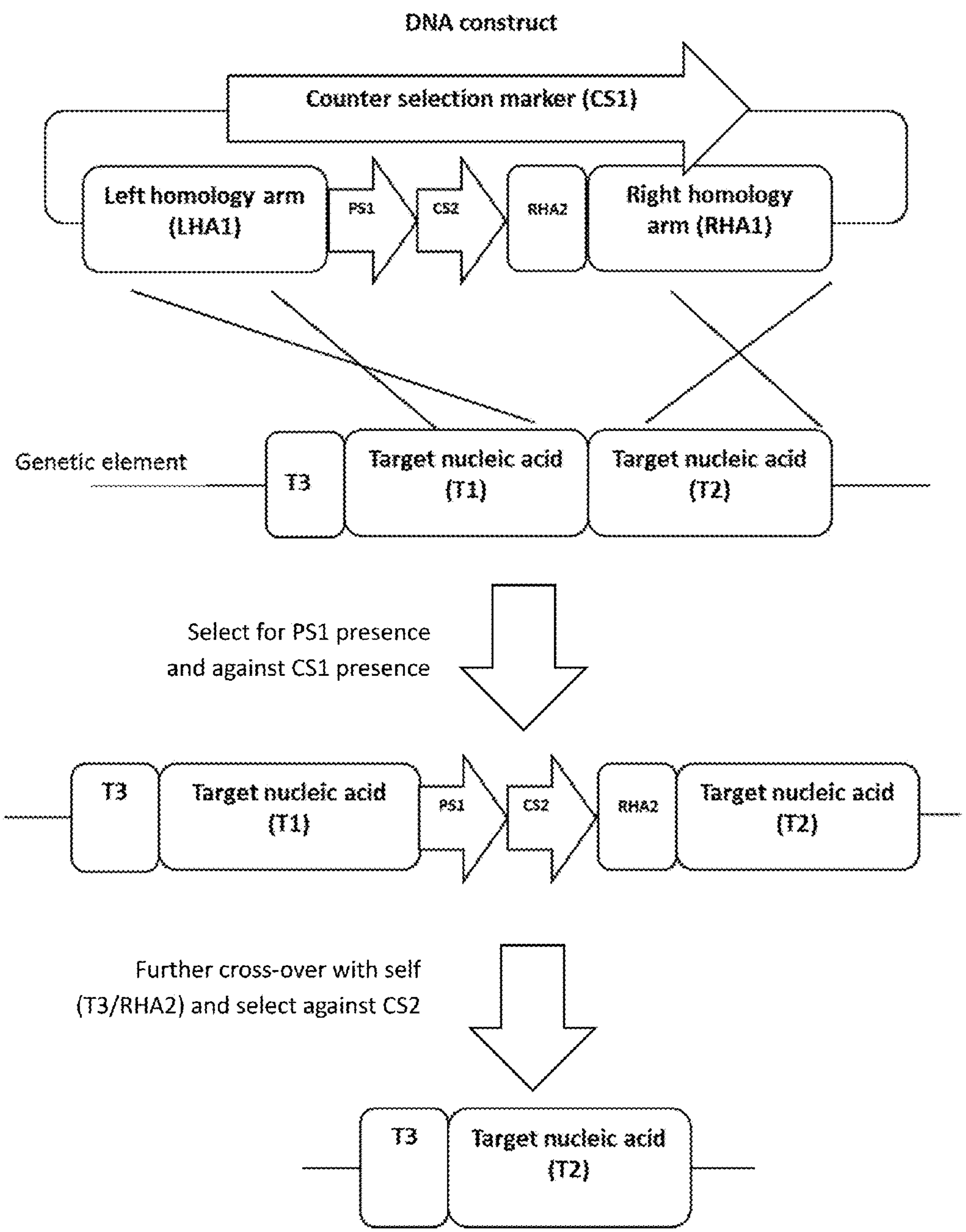
FIG. 1 is a diagram showing an embodiment in which a portion of DNA on a genetic element is deleted using a DNA construct.

The invention provides genetic tools to insert, replace, delete, or otherwise manipulate a nucleic acid sequence in a microorganism to produce a recombinant microorganism. Notably, the invention makes use of homologous recombination, a type of genetic recombination in which nucleotide sequences are exchanged between two similar or identical molecules of DNA. However, in contrast to classic approaches, which involve one positive and one negative selection marker with 2 homology arms, the invention generally utilizes one positive and two negative selection markers with three homology arms. As with classic approaches, the invention requires only two selection steps, but rather than screening for a first crossover in the first step and a second crossover with marker recycling in the second step, the invention forces a double crossover directly in the first step using a combination of a positive selection marker on an inserted nucleic acid and a selection negative marker on the construct backbone. In the second step, the selection markers may be recycled through the third homology arm and the second counter-selectable marker in a third crossover event. Since the invention involves three homologous recombination events it may be referred to as the "triple cross" method.

The invention provides a number of advantages over methods known in the art. For example, the invention allows modification of a genome at any site. In contrast, methods such as ACE are limited to modification of a genome at specific predetermined sites (e.g., at a pyrE/pyrF locus or at a site in a previously modified genome). The invention also allows for the integration, deletion, and/or mutation (e.g., frameshift, SNP) using a single system, while existing methods require the combination of multiple systems to achieve similar results, such as ClosTron/homologous recombination or FRT/Cre-Lox. The invention allows for "scarless" modification of a genome, leaving behind no artifacts such as residual base pairs or selection markers. Moreover, the invention requires no preparation or "priming" of the genome of the microorganism, such that it can be performed directly on a wild-type genome, in contrast to methods such as those described in Argyos, *Appl Environ Microbiol,* 77: 8288-8294, 2011. Additionally, the invention results in zero or minimal undesired integrations at non-target sites, which can be a problem with existing methods, such as ClosTron. Finally, the invention achieves nearly 100% efficiency under most conditions. In other words, nearly all of the microorganisms prepared and selected according to the invention exhibit the desired recombination, compared to as low as 10% efficiency for existing methods.

In general, the invention provides a method of producing a recombinant microorganism, comprising:

(a) providing a microorganism comprising a genetic element comprising a target nucleic acid T1, a target nucleic acid T2, and a target nucleic acid T3,
(b) providing a DNA construct comprising a left homology arm LHA1 homologous to T1, a right homology arm RHA1 homologous to T2, and a right homology arm RHA2 homologous to T3, wherein RHA2 is located between LHA1 and RHA1,
(c) allowing the genetic element of (a) to undergo homologous recombination with the DNA construct of (b), whereby T1 aligns with LHA1 and T2 aligns with RHA1 to insert the portion of the DNA construct between LHA1 and RHA1, including RHA2, into the genetic element between T1 and T2, and
(d) allowing the genetic element of (c) to undergo self-homologous recombination, whereby T3 aligns with RHA2 to remove the portion of the genetic element between T3 and RHA2.

Variations of this method may be used for inserting, replacing, deleting, or otherwise manipulating a nucleic acid sequence in a microorganism to produce a recombinant microorganism.

The invention may be used to delete a nucleic acid (e.g., T1) from a microorganism. In one embodiment, the invention provides a method of producing a recombinant microorganism, comprising:

(a) providing a microorganism comprising a genetic element comprising 5'-T3-T1-T2-3',
(b) providing a DNA construct comprising 5'-LHA1-RHA2-RHA1-3',
(c) allowing the genetic element of (a) to undergo homologous recombination with the DNA construct of (b), whereby T1 aligns with LHA1 and T2 aligns with RHA1 to insert the portion of the DNA construct between LHA1 and RHA1, including RHA2, into the genetic element between T1 and T2 to form a microorganism comprising a genetic element comprising 5'-T3-T1-RHA2-T2-3', and
(d) allowing the genetic element of (c) to undergo self-homologous recombination, whereby T3 aligns with RHA2 to remove the portion of the genetic element between T3 and RHA2 to form a microorganism comprising a genetic element comprising 5'-T3-T2-3', such that T1 is deleted from the genetic element.

This embodiment is shown in FIG. 1. Any base pairs located between RHA2 and RHA1 will be inserted into the genetic element. When RHA1 and RHA2 are immediately adjacent to each other on the DNA construct, this embodiment may be used to delete T1 without leaving any residual base pairs in the resulting DNA sequence. This process is referred to "scarless" deletion. The DNA construct may optionally contain one or more selection markers, such as CS1, PS1, and CS2. Selection against CS1 and for PS1 after step (c) selects for microorganisms with integration of the desired portion of the DNA construct into the genetic element. Selection against CS2 after step (d) selects for microorganisms that have undergone the desired self-homologous recombination. The portion of the DNA construct located between, but not including, LHA1 and RHA1 may be referred to as a nucleic acid cassette sequence (NS1). In FIG. 1, NS1 comprises 5'-PS1-CS2-RHA2-3'.

The invention may be used to replace a nucleic acid in a microorganism (e.g., T1) with a different nucleic acid (e.g., IS1). In one embodiment, the invention provides a method of producing a recombinant microorganism, comprising:

(a) providing a microorganism comprising a genetic element comprising 5'-T3-T1-T2-3',
(b) providing a DNA construct comprising 5'-LHA1-RHA2-IS1-RHA1-3' wherein IS1 is an insertion nucleic acid,
(c) allowing the genetic element of (a) to undergo homologous recombination with the DNA construct of (b), whereby T1 aligns with LHA1 and T2 aligns with RHA1 to insert the portion of the DNA construct between LHA1 and RHA1, including RHA2, into the genetic element between T1 and T2 to form a microorganism comprising a genetic element comprising 5'-T3-T1-RHA2-IS1-T2-3', and
(d) allowing the genetic element of (c) to undergo self-homologous recombination, whereby T3 aligns with RHA2 to remove the portion of the genetic element between T3 and RHA2 to form a microorganism comprising a genetic element comprising 5'-T3-IS1-T2-3', such that T1 is replaced by IS1 in the genetic element.

Figure 2:
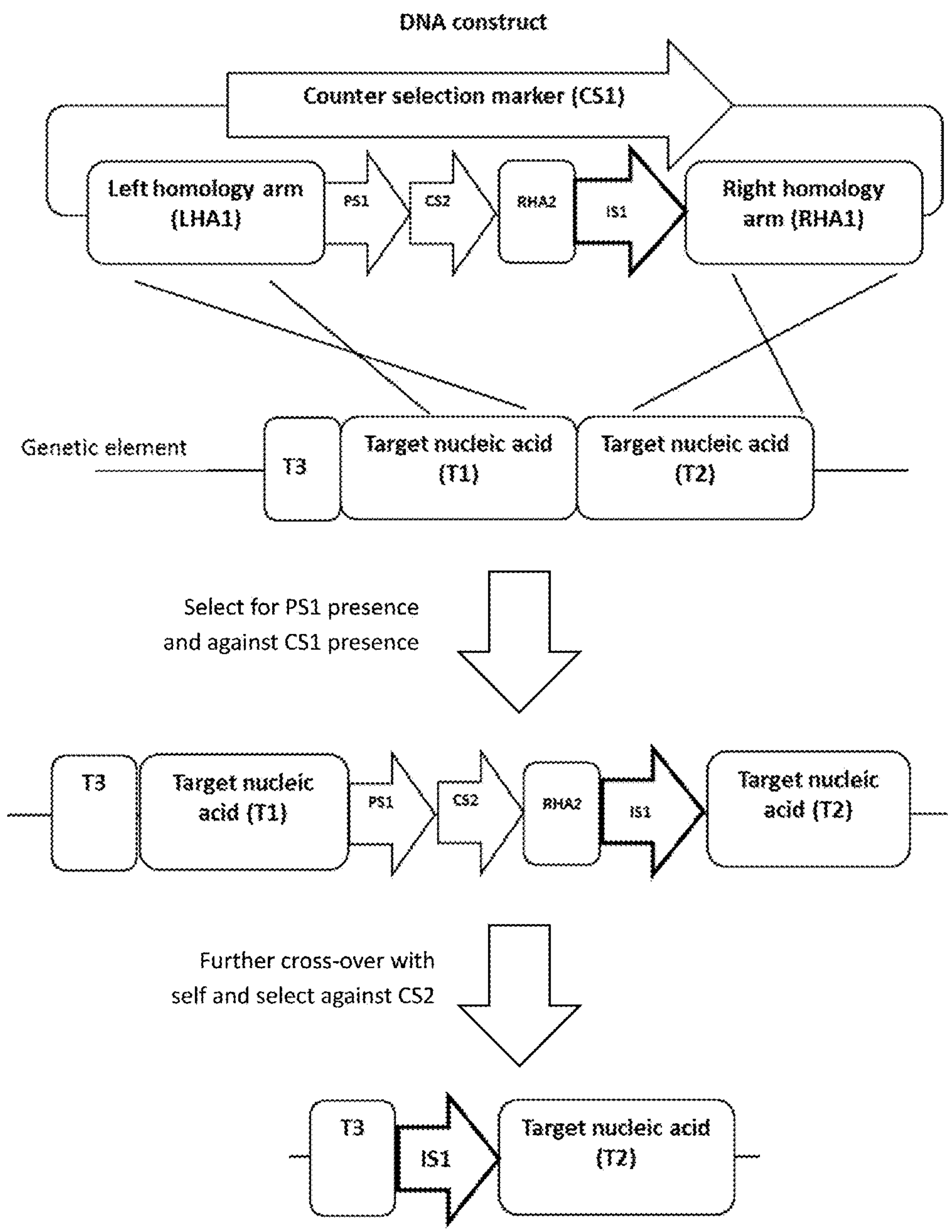
FIG. 2 is a diagram showing an embodiment in which a portion of DNA on a genetic element is deleted and replaced by an insertion sequence using a DNA construct.

This embodiment is shown in FIG. 2. Any base pairs located between RHA2 and RHA1 will be inserted into the genetic element. When IS1 is located immediately adjacent to RHA2 on the DNA construct, this embodiment may be used to delete T1 and simultaneously insert IS1 (i.e., replace T1 with IS1) without leaving any residual base pairs in the resulting DNA sequence (scarless). The DNA construct may optionally contain one or more selection markers, such as CS1, PS1, and CS2. Selection against CS1 and for PS1 after step (c) selects for microorganisms with integration of the desired portion of the DNA construct into the genetic element. Selection against CS2 after step (d) selects for microorganisms that have undergone the desired self-homologous recombination. The portion of the DNA construct located between, but not including, LHA1 and RHA1 may be referred to as a nucleic acid cassette sequence (NS1). In FIG. 2, NS1 comprises 5'-PS1-CS2-RHA2-IS1-3'.

In a variation of this embodiment, the intermediate microorganism comprising both T1 and IS1 may be retained by constant selection for PS1. This method enables observation of the effect of the T1 and IS1 on the phenotype of the microorganism. Constant selection for PS1 means that any microorganism that undergoes the third self-homologous recombination event will be unable to survive. In a particular embodiment, T1 is a gene whose expression leads to the production of one form of a product and IS1 comprises a gene whose expression leads to the production of a different form of the product. For example, the different forms of the product may be different stereoisomers, have different functional groups, or have different cofactor or substrate specificities. When the microorganism comprises a genetic element comprising both genes, the effects of having both products in the reaction mixture may be observed. In one embodiment, T1 encodes a gene which encodes the R stereoisomer of 2,3-butanediol and IS1 encodes a gene which encodes a meso-2,3-butanediol stereoisomer. The term "meso-2,3-butanediol" refers to both the (S,R) and (R,S) stereoisomers of 2,3-butanediol. When the genetic element comprises both genes, the effects of having both stereoisomers present in the reaction mixture may be observed. Removing the constant selection for PS1 will allow the microorganism to undergo the third self-homologous recombination event.

In another variation of this embodiment, a culture of microorganisms expressing T1 may be transitioned to lack expression of T1. Initially, T1 may be retained by selecting for PS1 and then, later, T1 may be deleted through self-homologous recombination by ceasing selection for PS1. A culture of microorganisms will transition from a population in which all microorganisms express T1, to a population in which some microorganisms express T1, to a population in which no microorganisms express T1. This will happen in a bioreactor over time if the deletion of T1 is not significantly detrimental to the growth of the microorganisms, even in the absence of a second counter selection step. If the deletion of T1 is detrimental to the growth of the microorganisms, then the microorganisms which retain T1 will outgrow the switched genotype and may remain the dominant strain in the reactor. When considering the size of the homology arms, RHA2 should be large enough to allow recombination with T3 at a high enough frequency to allow the transition from one genotype to the other over time. In addition however, RHA2 should be small enough that recombination will not happen frequently enough to kill a large proportion of cells when selecting for PS1. Generally, a RHA1/LHA1 size of about 1,000 bp coupled with an RHA2 size of about 300 bp provides a good balance of efficiency and cell growth. Selection for PS1 may be ceased at any desirable time. For example, selection for PS1 may be ceased when a culture reaches a particular cell density or a particular phase of growth (e.g., when the culture departs from stationary phase growth and enters exponential phase growth). As such, a gene may be deleted when it no longer confers a growth advantage, optimizing the use of resources.

Figure 7:
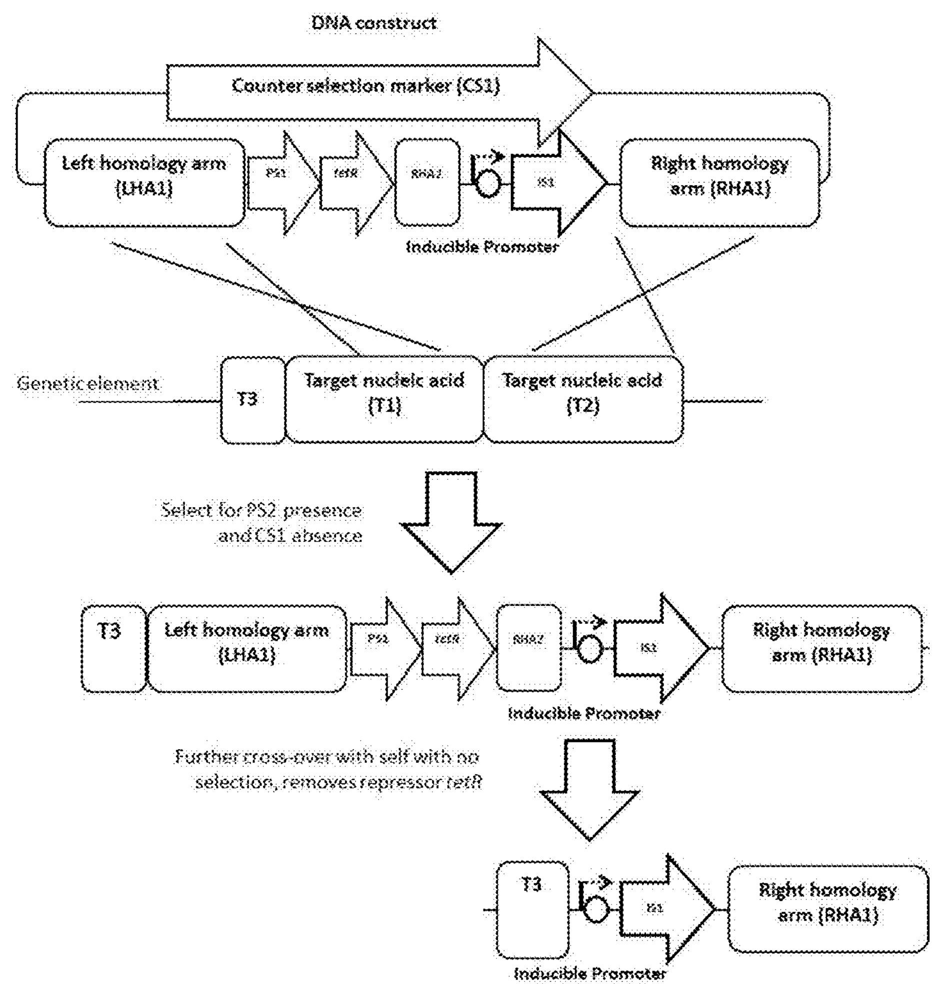
FIG. 7 is a diagram showing an embodiment in which a DNA construct and a repressor gene is integrated into a genetic element and where expression of the repressor gene is controlled by prolonged PS1 selection.
Figure 8:
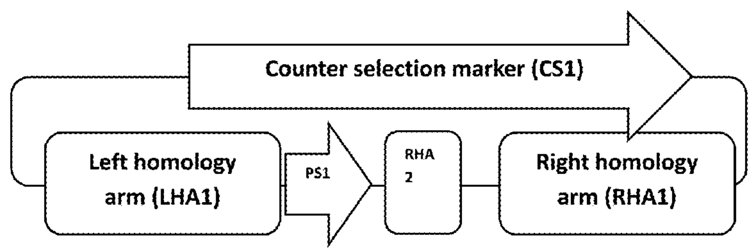
FIG. 8 is a diagram showing an embodiment in which the DNA construct is lacking a second counter selection marker.

The invention may also be used to repress a pathway using an inducible promoter system. In this embodiment, the DNA construct may comprise a repressor that is inserted into the genetic element of the microorganism as part of NS1. Selection for PS1 would select for microorganisms comprising NS1 (comprising the repressor). Ceasing selection for PS1 would allow the third self-homologous recombination event to occur, removing not only PS1, and optionally CS2, but also the repressor gene. This embodiment is in FIG. 7, where NS1 comprises LHA1, PS1, repressor tetR, RHA2, an inducible promoter repressed by tetR transcribing IS1 (a gene of interest), and RHA1.

The invention may be used to delete a nucleic acid (e.g., T4) from a microorganism. In one embodiment, the invention provides a method of producing a recombinant microorganism, comprising:

(a) providing a microorganism comprising a genetic element comprising 5'-$T1_{T3}$-T4-T2-3' wherein T1 encompasses T3 and T4 is a target nucleic acid, (b) providing a DNA construct comprising 5'-$LHA1_{RHA2}$-RHA2-RHA1-3' wherein LHA1 encompasses RHA2, (c) allowing the genetic element of (a) to undergo homologous recombination with the DNA construct of (b), whereby T1 ($T1_{T3}$) aligns with LHA1 ($LHA1_{RHA2}$) and T2 aligns with RHA1 to insert the portion of the DNA construct between LHA1 ($LHA1_{RHA2}$) and RHA1, including RHA2, into the genetic element between T1 ($T1_{T3}$) and T2 to form a microorganism comprising a genetic element comprising 5'-$T1_{T3}$-RHA2-T2-3', and (d) allowing the genetic element of (c) to undergo self-homologous recombination, whereby T3 aligns with RHA2 to remove the portion of the genetic element between T3 and RHA2 to form a microorganism comprising a genetic element comprising 5'-$T1_{T3}$-T2-3', such that T4 is deleted from the genetic element.

Figure 3:
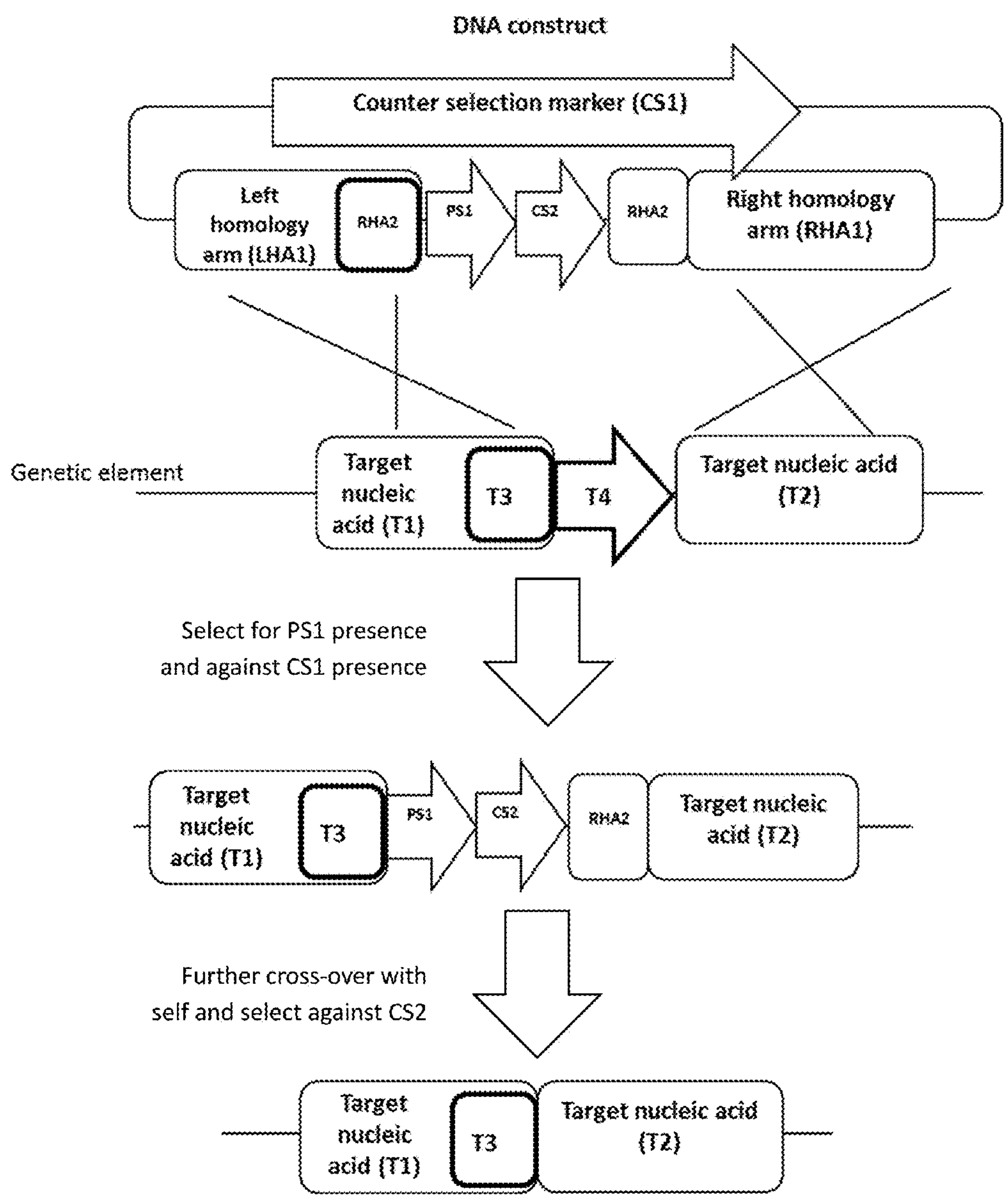
FIG. 3 is a diagram showing an embodiment in which a portion of DNA on a genetic element is deleted using a DNA construct.

This embodiment is shown in FIG. 3. The subscript on LHA1 ($LHA1_{RHA2}$) indicates that the sequence of LHA1 encompasses the sequence of RHA2, such that a portion of LHA1 (e.g., the 3' portion) is homologous to T3. The subscript on T1 ($T1_{T3}$) indicates that the sequence of T1 encompasses the sequence of T3, such that a portion of T1 (e.g., the 3' portion) is homologous to RHA2. The presence of these nested sequences allow for additional variations of the method of the invention. In particular, this embodiment allows for the deletion of T4 when it is flanked by T1 and T2 without deleting T1 or T2. Any base pairs located between RHA2 and RHA1 will be inserted into the genetic element. When RHA2 is immediately adjacent to RHA1 on the DNA construct, this embodiment may be used to delete T4 without leaving any residual base pairs in the resulting DNA sequence (scarless). The DNA construct may optionally contain one or more selection markers, such as CS1, PS1, and CS2. Selection against CS1 and for PS1 after step (c) selects for microorganisms with integration of the desired portion of the DNA construct into the genetic element. Selection against CS2 after step (d) selects for microorganisms that have undergone the desired self-homologous recombination. The portion of the DNA construct located between, but not including, LHA1 and RHA1 may be referred to as a nucleic acid cassette sequence (NS1). In FIG. 3, NS1 comprises 5'-PS1-CS2-RHA2-3'.

The invention may be used to insert a nucleic acid (e.g., IS1) into a microorganism. In one embodiment, the invention provides a method of producing a recombinant microorganism, comprising:

(a) providing a microorganism comprising a genetic element comprising 5'-$T1_{T3}$-T2-3' wherein T1 encompasses T3, (b) providing a DNA construct comprising 5'-$LHA1_{RHA2}$-RHA2-IS1-RHA1-3' wherein LHA1 encompasses RHA2 and IS1 is an insertion nucleic acid, (c) allowing the genetic element of (a) to undergo homologous recombination with the DNA construct of (b), whereby T1 ($T1_{T3}$) aligns with LHA1 ($LHA1_{RHA2}$) and T2 aligns with RHA1 to insert the portion of the DNA construct between LHA1 ($LHA1_{RHA2}$) and RHA1, including RHA2, into the genetic element between T1 ($T1_{T3}$) and T2 to form a microorganism comprising a genetic element comprising 5'-$T1_{T3}$-RHA2-IS1-T2-3', and (d) allowing the genetic element of (c) to undergo self-homologous recombination, whereby T3 aligns with RHA2 to remove the portion of the genetic element between T3 and RHA2 to form a microorganism comprising a genetic element comprising 5'-$T1_{T3}$-IS1-T2-3', such that IS1 is inserted in the genetic element.

Figure 4:
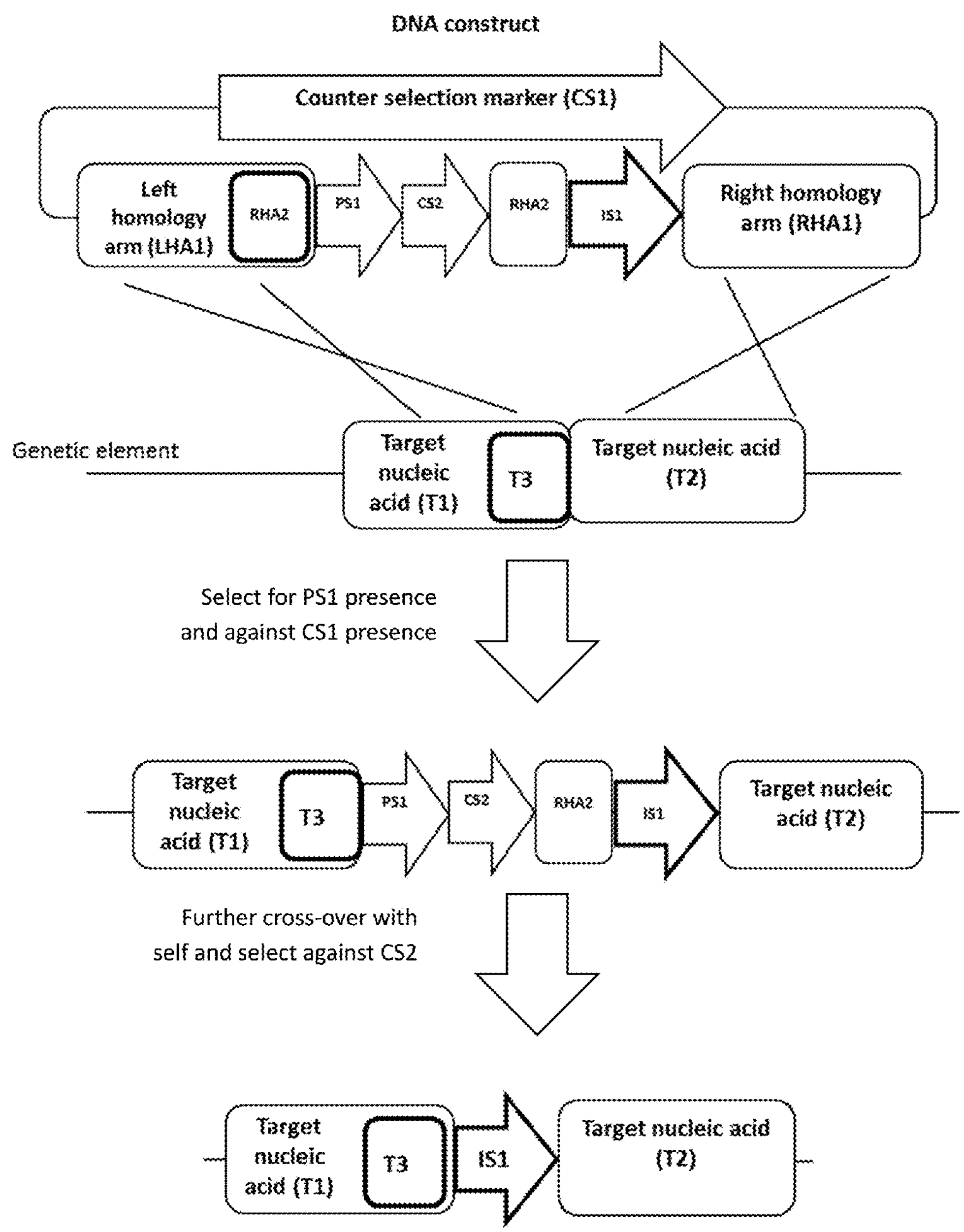
FIG. 4 is a diagram showing an embodiment in which a portion of DNA is inserted into a genetic element using a DNA construct.

This embodiment is shown in FIG. 4. The subscript on LHA1 ($LHA1_{RHA2}$) indicates that the sequence of LHA1 encompasses the sequence of RHA2, such that a portion of LHA1 (e.g., the 3' portion) is homologous to T3. The subscript on T1 ($T1_{T3}$) indicates that the sequence of T1 encompasses the sequence of T3, such that a portion of T1 (e.g., the 3' portion) is homologous to RHA2. The presence of these nested sequences allow for additional variations of the method of the invention. In particular, this embodiment allows for the insertion of IS1 without deleting T1. Any base pairs located between RHA2 and RHA1 will be inserted into the genetic element. When IS1 is located immediately adjacent to RHA2 on the DNA construct, this embodiment may be used to insert IS1 without leaving any residual base pairs in the resulting DNA sequence (scarless). The DNA construct may optionally contain one or more selection markers, such as CS1, PS1, and CS2. Selection against CS1 and for PS1 after step (c) selects for microorganisms with integration of the desired portion of the DNA construct into the genetic element. Selection against CS2 after step (d) selects for microorganisms that have undergone the desired self-homologous recombination. The portion of the DNA construct located between, but not including, LHA1 and RHA1 may be referred to as a nucleic acid cassette sequence (NS1). In FIG. 4, NS1 comprises 5'-PS1-CS2-RHA2-IS1-3'.

The invention may be used to replace a nucleic acid in a microorganism (e.g., T4) with a different nucleic acid (e.g., IS1). In one embodiment, the invention provides a method of producing a recombinant microorganism, comprising:

(a) providing a microorganism comprising a genetic element comprising 5'-$T1_{T3}$-T4-T2-3' wherein T1 encompasses T3 and T4 is a target nucleic acid, (b) providing a DNA construct comprising 5'-$LHA1_{RHA2}$-RHA2-IS1-RHA1-3' wherein LHA1 encompasses RHA2 and IS1 is an insertion nucleic acid, (c) allowing the genetic element of (a) to undergo homologous recombination with the DNA construct of (b), whereby T1 ($T1_{T3}$) aligns with LHA1 ($LHA1_{RHA2}$) and T2 aligns with RHA1 to insert the portion of the DNA construct between LHA1 ($LHA1_{RHA2}$) and RHA1, including RHA2, into the genetic element between T1 ($T1_{T3}$) and T2 to form a microorganism comprising a genetic element comprising 5'-$T1_{T3}$-RHA2-IS1-T2-3', and (d) allowing the genetic element of (c) to undergo self-homologous recombination, whereby T3 aligns with RHA2 to remove the portion of the genetic element between T3 and RHA2 to form a microorganism comprising a genetic element comprising 5'-$T1_{T3}$-IS1-T2-3', such that T4 is replaced by IS1 in the genetic element.

Figure 5:
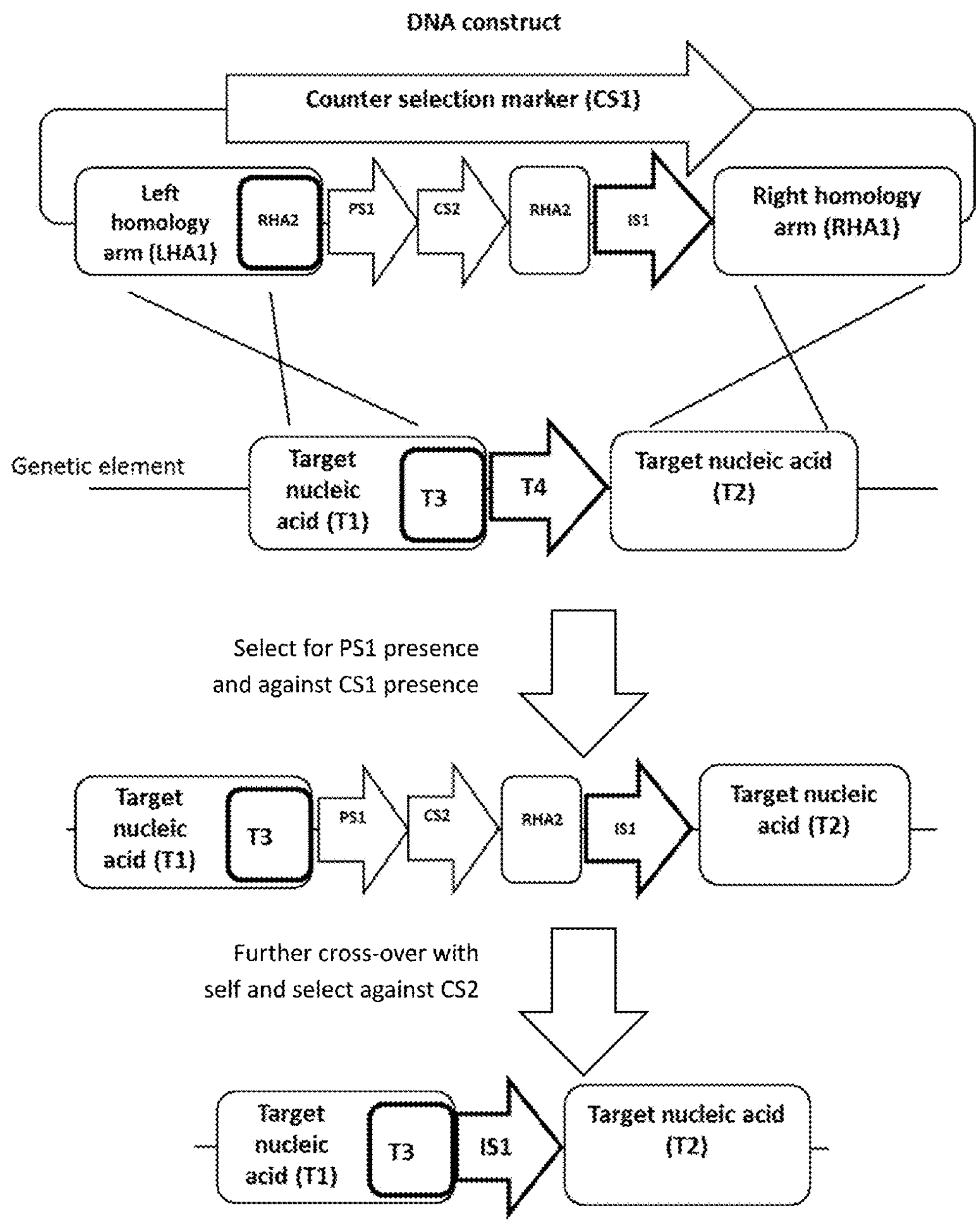
FIG. 5 is a diagram showing an embodiment in which a portion of DNA on a genetic element is deleted using a DNA construct.

This embodiment is shown in FIG. 5. The subscript on LHA1 ($LHA1_{RHA2}$) indicates that the sequence of LHA1 encompasses the sequence of RHA2, such that a portion of LHA1 (e.g., the 3' portion) is homologous to T3. The subscript on T1 ($T1_{T3}$) indicates that the sequence of T1 encompasses the sequence of T3, such that a portion of T1 (e.g., the 3' portion) is homologous to RHA2. The presence of these nested sequences allow for additional variations of the method of the invention. In particular, this embodiment allows for the deletion of T4 and the simultaneous insertion of IS1 (i.e., the replacement of T4 with IS1) in the genetic element. Any base pairs located between RHA2 and RHA1 will be inserted into the genetic element. When IS1 is located immediately adjacent to RHA2 on the DNA construct, this embodiment may be used to insert IS1 without leaving any residual base pairs in the resulting DNA sequence (scarless). The DNA construct may optionally contain one or more selection markers, such as CS1, PS1, and CS2. Selection against CS1 and for PS1 after step (c) selects for microorganisms with integration of the desired portion of the DNA construct into the genetic element. Selection against CS2 after step (d) selects for microorganisms that have undergone the desired self-homologous recombination. The portion of the DNA construct located between, but not including, LHA1 and RHA1 may be referred to as a nucleic acid cassette sequence (NS1). In FIG. 5, NS1 comprises 5'-PS1-CS2-RHA2-IS1-3'.

This embodiment has been found to have particular utility where the sequence to be deleted (T4) has high homology with the sequence to be inserted (IS1). If IS1 and T1 have high homology (e.g., if IS1 and T1 are genes encoding stereoisomers), a mixture of recombinant elements may be present—some with the correct sequence incorporated (IS1) and some with an undesirable cross over between IS1 and T1. Additionally, where the high homology sequence is longer than LHA1 or RHA1, the probability of the undesirable crossover will be higher due to the higher efficiency afforded by using a longer homologous sequence.

After the first and second homologous recombination events (i.e., after step (c)), this embodiment achieves high efficiency production of the desirable heteroduplexes, where RHA1 has crossed with T2 and LHA1 has crossed with T1. Where IS1 and LHA1 are of equal length, this embodiment, in theory, results in a crossover ratio between IS1 and RHA1 of 1:1. By PCR screening for the correct integration size, the crossover at LHA1 and RHA1) can be identified and used for the subsequent triple-crossover (allelic replacement). PCR may be useful in analysing any embodiment, but is of particular use where the genes share high homology.

In one embodiment, the methods of the invention may be performed iteratively. For example, the invention may be used to sequentially insert more than one insertion nucleic acid sequence (IS1, IS2, IS3, IS4, etc.) into the genetic element of a microorganism. This strategy allows for quick recycling of selection markers, making it possible to use previous selection markers to again in the next cycle. This embodiment provides considerable advantages over the prior art by dramatically reducing selection times and allowing quick sequential integration events. For example, using prior art methods, inserting three genes into a genome could take up to two weeks for each gene and cycles would be limited to the number of positive selection markers available. If only three markers were available, only three cycles of integration could be performed. The method of the invention, in contrast, requires only about six days per gene integration and allows cycles to be repeated indefinitely by reusing markers.

This embodiment is shown in FIGS. 6*a*-6*d*.

Figure 6A:
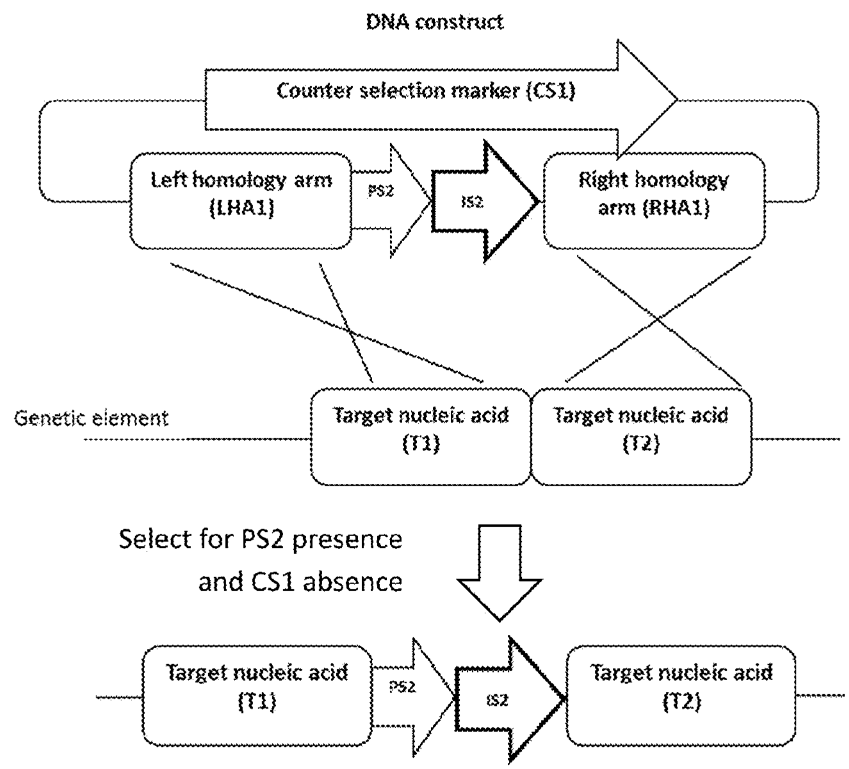
FIG. 6A is a diagram showing the first round of the multiple sequence insertion cycling strategy in which multiple portions of DNA are inserted into a genetic element using a DNA construct.

FIG. 6*a* shows the first round of insertions where IS2 and a PS2 are integrated into the genetic element by homologous recombination followed by selection for PS2 and against CS1. The designations PS2 and IS2 are used to distinguish the components used in this embodiment from the components used to in other embodiments.

Figure 6B:
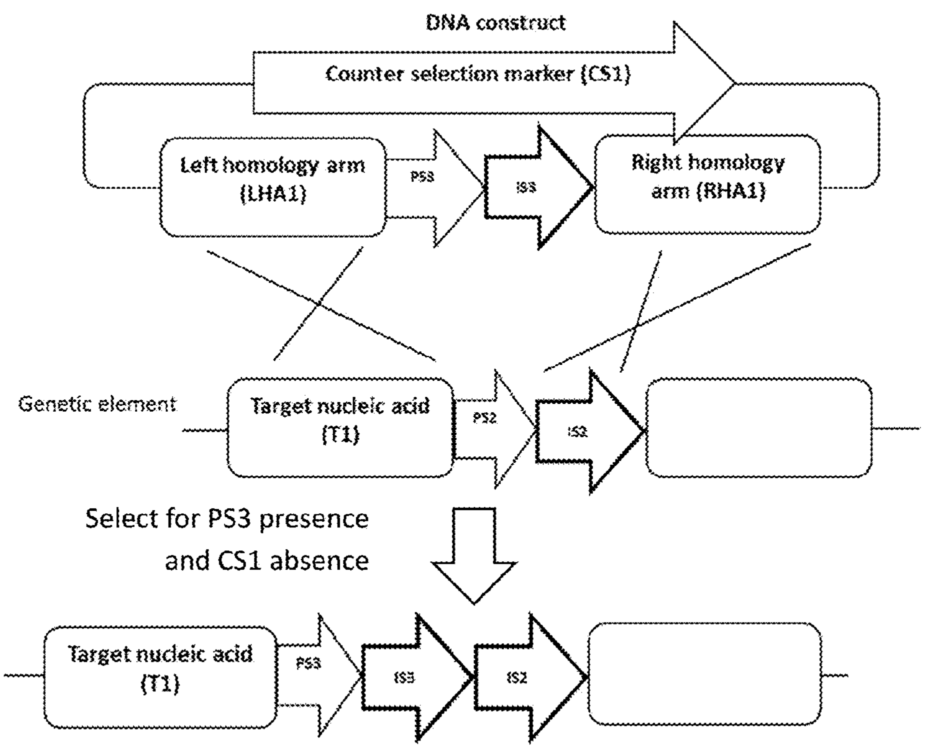
FIG. 6B is a diagram showing the second round of the multiple sequence insertion cycling strategy.

FIG. 6*b* shows the second round of insertions where the DNA construct comprises RH1 that is homologous to the earlier inserted sequence IS2. The DNA construct also comprises PS3 and IS3. A double crossover homologous recombination event occurs where LHA1 recombines with T1 and RHA1 recombines with IS2, resulting in a recombinant microorganism comprising the two inserted sequences as well as PS3. Selection for PS3 and against CS1 will result in a substantially pure culture of microorganisms with the desired insertion sequences. Although the designation CS1 is used here, it will be appreciated that a different counter selection marker may be used compared to the counter selection marker used in earlier rounds of this method.

Figure 6C:
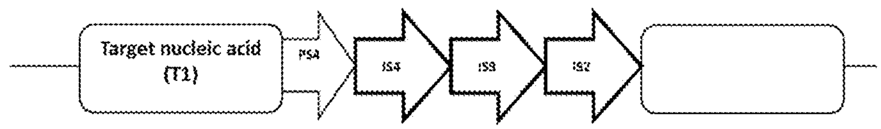
FIG. 6C is a diagram showing the third round of the multiple sequence insertion cycling strategy.

FIG. 6*c* shows the product of the third round of insertions, where IS4 and PS4 were present on the DNA construct (not shown).

Figure 6D:
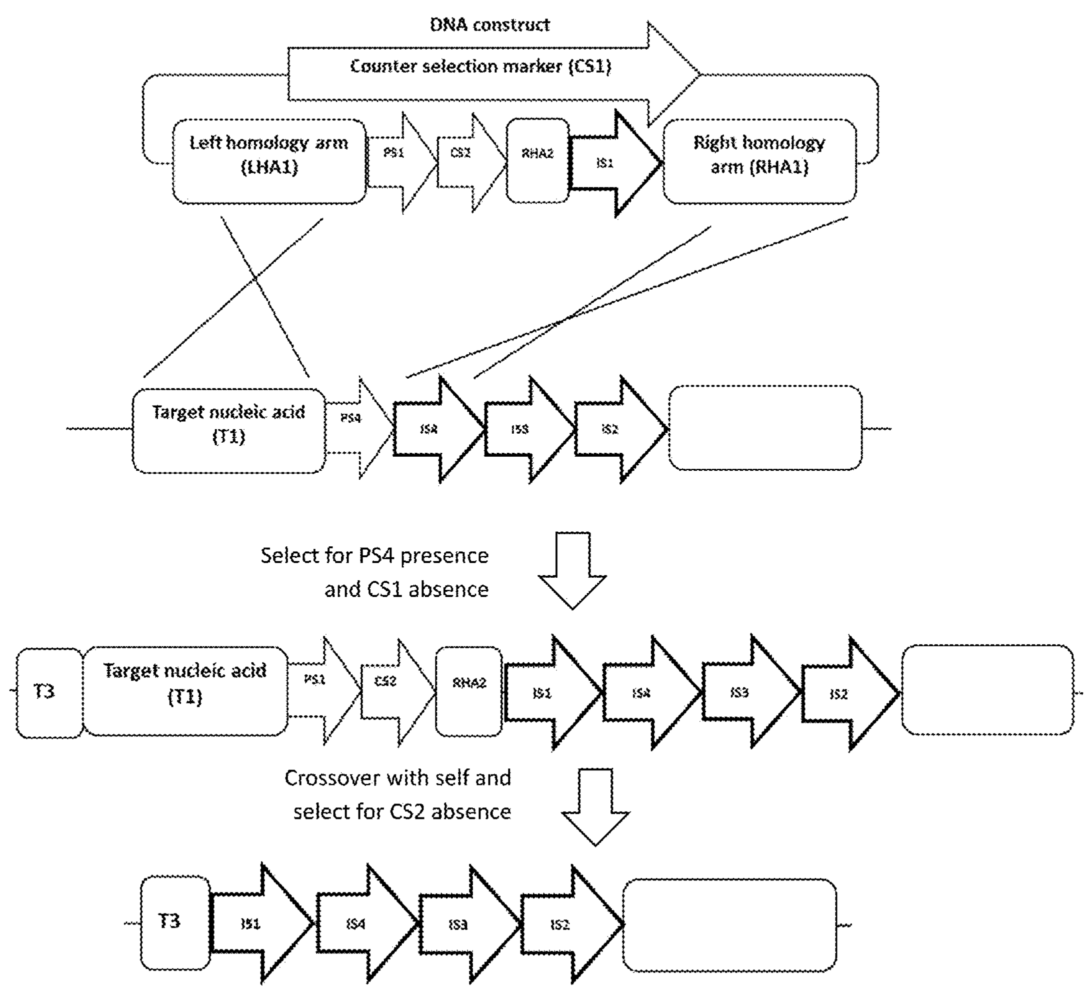
FIG. 6D is a diagram showing shows the final round of the multiple sequence insertion cycling strategy. In this embodiment, the final round comprises the insertion of a final sequence and removal of the marker and first target nucleic acid sequence.

FIG. 6*d* shows the final round of insertions, where RHA2 is inserted together with PS1 and CS2. RHA2 is homologous to a third target sequence T3 on the genetic element. A further insertion sequence IS1 is also shown. For this round, RHA1 is designed to be homologous to the last insertion sequence to be integrated (IS4). A homologous recombination event results in the integration of PS1, RHA2, IS1, and (optionally) CS2 to the genetic element. This sequence undergoes self-homologous recombination (i.e., RHA2 recombines with T3) to yield a microorganism with sequence T1 deleted and multiple sequences (IS1-4) inserted. Optional selection against CS2 enables isolation of microorganisms with the desirable integrations. Although FIGS. 6*a*-6*d* show the deletion of T1 and replacement with IS1-IS4, it will appreciated that any of the methods described herein may be performed in an iterative manner to achieve a desired deletion, insertion, replacement, or other manipulation of the genetic element.

The invention also provides a recombinant bacterium produced using the methods of the invention.

The invention further provides a kit for performing the methods of the invention. The kit may comprise, for example, a DNA construct and/or one or more compounds for selecting microorganisms expressing positive or counter selection markers.

Although there are disagreements in the literature about the exact process of initiation of homologous recombination, it is generally accepted that at least one of the strands on both the genetic element and DNA construct must be "nicked" and the double-stranded structure must unravel to some degree. This results in the homology arms (LHA1 and RHA1) and the target regions (T1 and T2) becoming single stranded and "exposed." The homology between the 3' strand on the genetic element and the complementary 5' strand on the DNA construct, or vice versa, results in complementary base pairing between LHA1:T1 and RHA1:T2. This process is sometimes known as "crossing-over" and results in a crossed strand intermediate known as a Holliday junction composed of the two double stranded nucleic acid molecules. The intermediate Holliday junction can be resolved by cutting and re-joining the crossed strands to yield recombinant and non-recombinant heteroduplexes.

The first homologous recombination event (recombination of LHA1 with T1) and second homologous recombination event (recombination of RHA1 with T2) is followed by a third (self) homologous recombination event within the resulting genetic element. In particular, the third homologous recombination event involves the recombination RHA2 with T3 to result in a further recombinant heteroduplex.

When the method of the invention is performed using a culture of microorganisms, the recombinant microorganisms containing a heteroduplex that has undergone a third homologous recombination event will eventually predominate in the population due to the natural instability caused by regions of homology on the genetic element and the associated tendency for homologous recombination to occur. Since the resultant heteroduplex lacks regions of homology, the third/final homologous recombination event is irreversible.

The term "genetic element" refers to a nucleic acid of a microorganism. Typically, the genetic element comprises double stranded DNA. The genetic element is typically located on a chromosome, plasmid, megaplasmid, or other extrachromosomal DNA within the microorganism. The genetic element may comprise, for example, a gene, a portion of a gene, a promoter region, an intergenic region, a noncoding region, a regulatory region, multiple genes, or any combination thereof. As described herein, the genetic element may comprise one or more nucleic acids defined as "T" (e.g., T1, T2, T3, T4).

The term "target nucleic acid" refers to nucleic acid sequence located within the genetic element. The target nucleic acid may comprise, for example, a gene, a portion of a gene, a promoter region, an intergenic region, a noncoding region, a regulatory region, multiple genes, or any combination thereof. As described herein, target nucleic acids may include one or more of T1, T2, T3, T4, etc. Specifically, T1 is a target nucleic acid on the genetic element homologous to LHA1, T2 is a target nucleic acid on the genetic element homologous to RHA1, and T3 is a target nucleic acid on the genetic element homologous to RHA2.

The term "DNA construct" refers to a nucleic acid designed to undergo homologous recombination with the genetic element. Typically, the DNA construct is double stranded DNA. In one embodiment, the DNA construct is a plasmid or a vector. The DNA construct may contain nucleic acid regions and/or selection markers. As described herein, the genetic element may comprise one or more nucleic acids defined as LHA (e.g., LHA1), RHA (e.g., RHA1, RHA2), and IS (e.g., IS1, IS2, IS3, IS4). Specifically, LHA1 is a left homology arm on the DNA construct homologous to T1, RHA1 is a right homology arm on the DNA construct homologous to T2, and RHA2 is a right homology arm on the DNA construct homologous to T3. The DNA construct may comprise one or more selection markers defined as CS (e.g., CS1, CS2) and PS (e.g., PS1). Additionally, the DNA construct may comprise one or more regulatory elements, origins of replication, or multicloning sites. The DNA construct may be a naked nucleic acid, a methylated or unmethylated nucleic acid, or a nucleic acid formulated with one or more agents to facilitate delivery to the microorganism. Furthermore, the DNA construct may be replicating or non-replicating.

The "backbone" of the DNA construct refers to a portion of the DNA construct designed to be excluded from homologous recombination or integration events. In one embodiment, the backbone construct comprises a counter selection marker to allow selection against microorganisms in which the backbone was integrated. The backbone may contain a Gram-negative replicon to allow plasmid replication in Gram-negative bacteria. Additionally or alternatively, the backbone may contain a Gram-positive replicon to allow plasmid replication in Gram-positive bacteria. In one embodiment, the backbone contains both Gram-positive and Gram-negative replicons to allow plasmid replication in both Gram-positive and Gram-negative bacteria.

The DNA construct may be described as comprising a "nucleic acid cassette sequence," which refers to the portion of the DNA construct between, but not including, LHA1 and RHA1. For example, the nucleic acid cassette sequence may comprise 5'-RHA2-3' or 5'-RHA2-IS1-3' or 5'-PS1-RHA2-3' or 5'-PS1-CS2-RHA2-3' or the like, depending on the embodiment. Typically, RHA1 is located immediately adjacent to the 3' end of the nucleic acid cassette sequence and LHA1 is located immediately adjacent to the 5' end of the nucleic acid cassette sequence.

The term "homology arm" refers to a portion of the DNA construct that allows for homologous recombination between the DNA construct and the genetic element. Typically, homology arms are located on an artificial plasmid that undergoes homologous recombination with a bacterial host chromosome. The homology arms preferably have 100% complementarity to target regions on the genetic element. However, the homology arms may have less than 100% complementarity to target regions on the genetic element, as long as they have sufficient complementarity to allow for homologous recombination. Appropriate homology arms may be designed based on publically available sequence information for a given target microorganism.

The size of the homology arms may affect the efficiency of the methods of the invention.

In one embodiment, RHA2 comprises fewer base pairs than LHA1 and RHA1, which increases the probability that the desired LHA1/T1 and RHA1/T2 recombinations will occur. Although a smaller RHA2 reduces the probability that the desired RHA2/T3 recombination will occur, positive and counter selection steps ensure a sufficient number of microorganisms undergo all desired recombination steps. Since the final recombination is stable and irreversible, a population of microorganisms will naturally move towards this equilibrium. Integration of CS2 into the genetic element allows for selection against cells that have not undergone the RHA2/T3 recombination. If all homology arms are the same length, RHA2/T3 recombination will occur with approximately the same frequency as LHA1/T1 and RHA1/T2 recombination, such that large percentage of the microorganisms (~50%) will not integrate PS1 or CS2 due to RHA2/T3 recombination instead of LHA1/T1 and RHA1/T2 recombination. These microorganisms will then be killed by subsequent selection steps.

In one embodiment, there is an increased base pair ratio between RHA2 and either RHA1 or LHA1 (expressed herein as RHA2:RHA1 or RHA2:LHA1) when compared to the LHA1:RHA1 ratio and this higher ratio will, up to a point, result in the LHA1/RHA1 crossover being favored. In a particular embodiment, RHA2 comprises approximately one third of the number of base pairs of either LHA1 or RHA1, i.e., the ratio of base pairs for RHA2:RHA1 or RHA2:LHA1 is approximately 1:3.

In one embodiment, at least one of LHA1 and RHA1 comprise a nucleic acid sequence of approximately 50 bp to 4,000 bp. In a preferred embodiment, RHA1 and LHA1 comprise approximately 1,000 bp. In general, the longer the homology arm, the greater the efficiency of recombination. Homology arms of approximate length of 1,000 bp or greater facilitate efficient homologous recombination and selection while still allowing the nucleic acid cassette sequence of DNA construct to be suitably large. The size of the homology arms could be increased to 2,000 bp or more, although increasing the size of the homology arms increases the size of the plasmid as a whole, which limits the size of other nucleic acids in the DNA construct, such as the nucleic acid cassette sequence.

When RHA2 is shorter than the other homology arms, LHA1 and RHA1 will have a higher frequency of correct integration due to the higher recombination probability/efficiency for larger homology arms. Thus, a higher portion of the cells will integrate the positive and counter selection markers into the genetic element and subsequently survive the selection processes. Although any length of RHA2 could theoretically be used, a size of approximately 50-500 bp is preferable. For example, RHA2 may be approximately 300 bp in length.

In the absence of a difference in the length of RHA2, a three-step selection process may be required to obtain a substantially pure culture of the recombinant microorganism in a reasonable timeframe. This process may include PS1 selection, PS1 selection+CS1 counter selection, and CS2 counter selection. The PS1 selection step is generally required to enrich the culture in desired recombinants to achieve the higher cell density required to overcome the lower frequency of correct recombination. However, if there is a reasonably high initial probability of correct recombination resulting in a culture with a higher frequency of cells having undergone the correct double-crossover, this step may be omitted. Accordingly, the process may include only PS1 selection+CS1 counter selection and CS2 counter selection.

Figure 9:
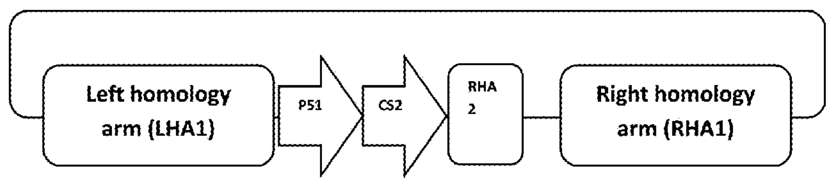
FIG. 9 is a diagram showing an embodiment in which the DNA construct comprises a non-replicating plasmid and lacks the first counter selection marker.
Figure 10:
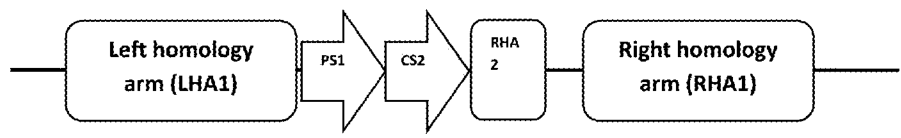
FIG. 10 is a diagram showing an embodiment in which the DNA construct comprises transforming linear DNA and lacks the first counter selection marker.

In one embodiment, the DNA construct is a non-replicating plasmid, e.g., a suicide vector. Suicide vector systems are well known in the art and allow for direct selection for gene replacement in Gram-negative bacteria (Quandt, *Gene,* 127: 15-21, 1993). As shown in FIG. 9, the DNA construct may be designed such that any microorganism which does not incorporate a nucleic acid cassette sequence (e.g., NS1) comprising at least PS1 and RHA2 will be unable to survive and/or reproduce. In another embodiment, as shown in FIG. 10, the DNA construct comprises linear DNA. In these embodiments, CS1 is not required because selection for PS1 allows for efficient selection of microorganisms comprising the desired nucleic acid sequence cassette.

The DNA construct may comprise one or more selection markers, which confer a trait or traits suitable for artificial selection and indicate the success of a transfection or other procedure meant to introduce foreign DNA into a cell. The selection markers may be positive selection markers (PS), which confer selective advantage to the host microorganism (e.g., antibiotic resistance, which allows the host microorganism to survive antibiotic selection). Alternatively, or additionally, the selection markers may be counter selection markers (CS), which eliminate or inhibit growth of the host microorganism upon selection (e.g., thymidine kinase, which makes the host microorganism sensitive to ganciclovir selection). The selection markers may be codon optimized for expression in a particular genus or species, e.g., *Clostridium* or *Clostridium autoethanogenum*. Positive and counter selection markers and positive and counter selection methods are well known in the art.

The positive selection marker may be chosen from any positive selection marker known in the art. For example, the positive selection marker(s) may be independently selected from the group consisting of catP, tetA(C), tetM, aad9, aadA, aadA2, and ermB. However, the positive selection marker may also be any other antibiotic resistance marker, toxin/antitoxin cassette, essential gene (e.g., thiamine biosynthesis or uracil biosynthesis genes), etc. The sequences of positive selection markers are generally publically available. For example, GenBank WP_002570989 provides the sequence of catP, GenBank YP_007078965 provides the sequence of ermB, and GenBank NP_957551.1 provides the sequence of tetA. Microorganisms expressing positive selection markers may be identified and selected using any method known in the art. For example, microorganisms may be cultured in or on a medium that contains a toxin (e.g., an antibiotic) which kills microorganisms that do not express the positive selection marker (e.g., an antibiotic resistance gene/protein). The positive selection marker may be located in the nucleic acid cassette sequence, such that it is possible to select for microorganisms wherein the nucleic acid cassette sequence of the DNA construct successfully integrated into the genetic element of the microorganism.

The counter selection marker may be chosen from any counter selection marker known in the art. For example, the counter selection marker(s) may be independently selected from the group consisting of pheS*, upp, sacB, tetAR, thyA, ccdB, lacY, rpsL, codA, pyrE, HSTK (thiK), gatA-1, and mazF. The counter selection marker may be any antitoxin component from a bacterial toxin anti-toxin system, wherein the microorganism may comprise a toxin gene wherein a corresponding antitoxin gene is essential for the microorganism's survival. In one embodiment, the antitoxin gene may be introduced in a toxin-positive microorganism, wherein the antitoxin gene is selected for until the toxin gene is no longer present. In one embodiment, the DNA construct comprises at least two different counter selection markers to expedite the isolation and selection of a culture with a homogenous genotype. Microorganisms expressing counter selection markers may be identified and selected using any method known in the art. For example, microorganisms may be cultured in or on a medium that contains a component which is toxic only to those microorganisms which express the counter selection marker. In one embodiment, the counter selection marker is HSTK and the counter selection method involves culturing microorganisms in or on a medium containing a guanosine analogue, such as ganciclovir. Microorganisms that contain and express a nucleic acid encoding HSTK will not survive in the presence of the guanosine analogue. Accordingly, the microorganisms that survive are selected as not expressing HSTK.

PheS is the alpha subunit of the two-subunit protein phenylalanine tRNA synthetase, which is responsible for aminoacylation of $tRNA^{Phe}$ with phenylalanine, a process that is critical for protein production in a microorganism. The enzyme catalyzes the acylation of phenylalanine to its cognate tRNA. The resultant $tRNA^{Phe}$ is delivered to a ribosome by elongation factors then subsequently bound to its cognate anti-codon present on the mRNA. Once bound, the amino acid is covalently attached to its preceding amino acid, thereby increasing the peptide chain.

pheS* encodes a modified PheS protein with a single base pair change from the wild-type pheS, resulting in an amino acid substitution. Full details of the modified pheS* gene, protein, and method of use/production are described in U.S. Patent Application 61/877,272, the entirety of which is incorporated herein by reference. In one embodiment, the PheS* is derived from *C. autoethanogenum* and has the amino acid sequence of SEQ ID NO: 2 and the nucleic acid sequence of SEQ ID NO: 1. A modified PheS* has the sequence of SEQ ID NO: 3. Functionally equivalent variants of pheS* or PheS* may also be used.

When using PheS* as a counter selection marker, selection for microorganisms which do not express PheS* involves culturing the microorganisms in or on a medium containing p-chlorophenylalanine or another phenylalanine analogue. In one embodiment, the phenylalanine analogue is chosen from chlorophenylalanine, fluorophenylalanine, and bromophenylalanine. In one embodiment, the phenylalanine analogue is chosen from DL-4-chlorophenylalanine, p-chlorophenylalanine, p-fluoro-L-phenylalanine, p-fluoro-DL-phenylalanine, and p-bromo-L-phenylalanine Microorganisms that contain and express a nucleic acid encoding PheS* will not survive in the presence of the p-chlorophenylalanine or phenylalanine analogue.

HSTK is a protein that catalyzes the reaction: Thd+ ATP→TMP+ADP, wherein Thd is deoxythymidine, ATP is adenosine 5'-triphosphate, TMP is deoxythymidine 5'-phosphate, and ADP is adenosine 5'-diphosphate. HSTK may also be referred to as HS-tk, HSTK, HStk and thiK, all of which refer to the same protein. HSTK catalyzes the phosphorylation of deoxythymidine. The HSTK may be derived from any appropriate organism. For example, the HSTK may be derived from herpes simplex virus 1 or herpes simplex virus 2 (HS-TK), VZV, CMV, HHV7, HHV7, HHV8, or EBV. Alternatively, HSTK may be a functionally equivalent variant any of these HSTK proteins. HSTK proteins include those described in public databases such as GenBank (e.g., GenBank AB009254.2). In one embodiment, the HSTK comprises the amino acid sequence of SEQ ID NO: 5 and nucleic acid sequence of SEQ ID NO: 4. Functionally equivalent variants of hstk or HSTK may also be used.

The selection markers may be under the control of one or more promoters. The promoter may located within a nucleic acid encoding the selection marker or the promoter may be separated from the nucleic acid encoding the selection marker by intervening nucleotides. The promoter may be constitutive or inducible. Any promoter know in the art may be used. For example, the promoter may be a T7 bacteriophage promoter, T3 bacteriophage promoter, T5 bacteriophage promoter, a bacterial promoter, a synthetic promoter, or any other promoter. In one embodiment, the DNA construct comprises a strong promoter that drives expression of the selection marker(s), e.g., a T3 promoter, a T7 promoter, a PrRNA promoter, a Ptrc promoter, or any other strong promoter. In addition to the promoter, the DNA construct may comprise other regulatory elements, such as operators and/or enhancers.

Selection steps may be performed simultaneously or consecutively. For example, microorganisms with a single crossover event could be selected using a positive selection maker and, subsequently, microorganisms with a double crossover event could be selected using a counter selection marker. Alternatively, positive and counter selection could be performed simultaneously. Where the positive selection marker is positioned on the DNA construct outside of the homology arms (in the backbone of the DNA construct), microorganisms with a single crossover event could be selected using a positive selection maker and, subsequently, microorganisms with a double crossover event could be selected using a counter selection marker. Where the positive selection marker is positioned on the DNA construct between the homology arms (in the nucleic acid cassette sequence), positive selection and counter selection may be performed simultaneously, since any microorganism that has the positive selection marker integrated into its genetic element and is resistant to the counter selection marker will have undergone a double crossover event.

In one embodiment, the DNA construct comprises a counter selection marker CS1. Preferably, CS1 is located on the backbone of the DNA construct. Selection against CS1 selects for microorganisms with the desirable components of the construct incorporated only (e.g., the nucleic acid sequence cassette, but not the backbone of the DNA construct). FIGS. 1-5 show a DNA construct comprising CS1 located on the backbone of the DNA construct.

In one embodiment, the DNA construct further comprises counter selection marker CS2. Preferably, CS2 is located between LHA1 and RHA2. FIGS. 1-5 show a DNA construct comprising CS2 located on the DNA construct between LHA1 and RHA2.

In one embodiment, the DNA construct comprises a positive selection marker PS1. Preferably, PS1 is located between LHA1 and RHA2.

In one embodiment, the DNA construct comprises counter selection markers CS1 and CS2 and a positive selection marker PS1. Preferably, CS1 is located upstream of LHA1 (in the backbone of the DNA construct) and CS2 and PS1 are located between LHA1 and RHA2. CS2 and PS1 may be arranged in any order. For example, the DNA construct may comprise 5'-CS2-PS1-3' or 5'-PS1-CS2-3'. In one embodiment, the step of allowing the genetic element of to undergo homologous recombination with the DNA construct is followed by a step of selecting for expression of PS1 and against expression of CS1 and the step of allowing the genetic element of to undergo self-homologous recombination is followed by a step of selecting against expression of CS2. In this embodiment, CS2 is incorporated into the intermediate microorganism, but is lost in the final microorganism.

It will be appreciated that the inclusion of CS2 on the DNA construct is not essential to enable the method to yield a recombinant microorganism of the invention, as the irreversible nature of the third/final homologous recombination event dictates that the recombinant microorganism lacking homologous regions will eventually predominate anyway.

It will be appreciated that the order of the components (e.g., LHA1, RHA1, RHA2, PS1, CS1, CS2) on the DNA construct is variable. Typically, the DNA construct comprises the components ordered, e.g., 5'-LHA1-RHA2-RHA1-3'. However, the order of the components may be reversed, e.g., 5'-RHA1-RHA2-LHA1'-3'. If the genetic element comprises, e.g., 5'-T1-T2-T3-3', the reversal of the components of the DNA construct will result in the deletion/replacement of T2 instead of T1.

Moreover, unlike the order of the homology arms, the order of the positive and counter selection markers is not essential to the functionality of the system. The DNA construct may comprise PS1 and CS2 in either order, e.g., 5'-PS1-CS2-3' or 5'-CS2-PS1-3'.

In one embodiment, the DNA construct further comprises at least one insertion nucleic acid sequence defined as IS (e.g., IS1, IS2, IS3, IS4, etc.) for integration into the genetic element. The insertion nucleic acid sequence may include, for example, one or more genes, promoters, regulatory sequences, or other genetic elements and may be coding or noncoding. It may include a nucleic acid sequence designed to introduce a genetic modification to a target nucleic acid sequence in the genetic element, including a deletion, addition, or substitution of one or more nucleotides. In some embodiments, the insertion nucleic acid sequence may be designed to result in the deletion of a gene present in the genetic element, for example, by the association of the gene with the insertion nucleic acid sequence for downstream deletion process steps.

Figure 11:
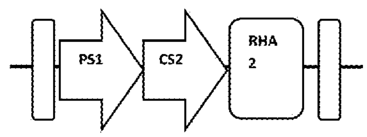
FIG. 11 is a diagram showing an embodiment in which the DNA construct comprises shorter homology arms appropriate for use in the lambda-red recombination system.

In one embodiment, one or more of the homologous recombination events proceed according to the bacteriophage lambda red recombination system (Murphy, *J Bacteriol,* 180: 2063-2071, 1998 and Murphy, *Gene,* 246: 321-330, 2000). Using this system to integrate the desired cassette into the genetic element results in high integration efficiency and eliminates the need for CS1, since the DNA will be linear. Also, the LHA1 and RHA1 homology arms need only be 30-70 bp long. FIG. 11 shows a DNA construct comprising homology arms appropriate for use in the lambda red recombination system. Exemplary methods and protocols for use of the lambda red recombination system are known in the art (Sharan, *Nat Protoc,* 4: 206-223, 2009).

“Endogenous” refers to a nucleic acid or protein that is present or expressed in the wild-type or parental microorganism from which the recombinant microorganism of the invention is derived. For example, an endogenous gene is a gene that is natively present in the wild-type or parental microorganism from which the recombinant microorganism of the invention is derived. In one embodiment, the expression of an endogenous gene may be controlled by an exogenous regulatory element, such as an exogenous promoter.

“Exogenous” refers to a nucleic acid or protein that is not present in the wild-type or parental microorganism from which the microorganism of the invention is derived. In one embodiment, an exogenous gene or enzyme may be derived from a heterologous strain or species and introduced to or expressed in the microorganism of the invention. In another embodiment, an exogenous gene or enzyme may be artificially or recombinantly created and introduced to or expressed in the microorganism of the invention. Exogenous nucleic acids may be adapted to integrate into the genome of the bacterium of the invention or to remain in an extra-chromosomal state in the microorganism of the invention, for example, in a plasmid.

“Mutated” refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

The term “genetic modification” broadly refers to manipulation of the genome or nucleic acids of a microorganism. Methods of genetic modification of include heterologous gene expression, gene or promoter insertion or deletion, altered gene expression or inactivation, enzyme engineering, directed evolution, knowledge-based design, random mutagenesis methods, gene shuffling, and codon optimization. Such methods are described, for example, in Sambrook, Molecular Cloning: A Laboratory Manual, Cold Spring Harbor Laboratory Press, Cold Spring Harbor, N.Y., 2001; Pleiss, *Curr Opin Biotechnol,* 22: 611-617, 2011; Park, Protein Engineering and Design, CRC Press, 2010.

The term “variants” includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as “functionally equivalent variants.” By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum, Clostridium beijerinckii*, or *Clostridium ljungdahlii*, the details of which are publicly available on websites such as Genbank or NCBI. Functionally equivalent variants also includes nucleic acids whose sequence varies as a result of codon optimization for a particular organism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

A functionally equivalent variant of a selection marker exemplified herein need not have the same level of activity as the selection marker of which it is a variant. All that is required is that some level of the desired activity is retained. Assays for assessing the activity of selection markers exemplified herein are known in the art. For example, the function or activity of pheS* can be tested by measuring aminoacylation. Velocities of aminoacylation and kinetic parameters of pheS* may be used to test activity variations of pheS* in utilising phenylalanine (Kast, *J Mol Biol,* 222: 99-124, 2991).

Nucleic acids, including the DNA construct, may be delivered to a microorganism of the invention using any method known in the art. For example, nucleic acids may be delivered as naked nucleic acids or may be formulated with one or more agents (e.g., liposomes). The nucleic acids may be DNA, RNA, cDNA, or combinations thereof, as is appropriate. Restriction inhibitors may be used in certain embodiments (Murray, *Microbiol Molec Biol Rev,* 64: 412-434, 2000). Additional vectors may include plasmids, viruses (including bacteriophage), cosmids, and artificial chromosomes.

By way of example, transformation (including transduction or transfection) of the DNA construct or other nucleic acids may be achieved by electroporation, ultrasonication, polyethylene glycol-mediated transformation, chemical or natural competence, protoplast transformation, prophage induction, or conjugation (see, e.g., Molecular Cloning: A Laboratory Manual, Cold Spring Harbor Laboratory Press, Cold Spring Harbor, N.Y., 1989). The use of electroporation has been reported for several carboxydotrophic acetogens, including *Clostridium ljungdahlii* (Koepke, *PNAS,* 107: 13087-13092, 2010; WO/2012/053905), *Clostridium autoethanogenum* (WO/2012/053905), *Clostridium aceticum* (Schiel-Bengelsdorf, *Synthetic Biol,* 15: 2191-2198, 2012), and *Acetobacterium woodii* (Strätz, *Appl Environ Microbiol,* 60: 1033-1037, 1994). The use of electroporation has also been reported in Clostridia, including *Clostridium acetobutylicum* (Mermelstein, *Biotechnol,* 10: 190-195, 1992), and *Clostridium cellulolyticum* (Jennert, *Microbiol,* 146: 3071-3080, 2000). Prophage induction has been demonstrated for carboxydotrophic acetogens, including *Clostridium scatologenes* (Parthasarathy, Development of a Genetic Modification System in *Clostridium scatologenes* ATCC 25775 for Generation of Mutants, Masters Project, Western Kentucky University, 2010), and conjugation been described for many Clostridia, including *Clostridium difficile* (Herbert, *FEMS Microbiol Lett,* 229: 103-110, 2003) and *Clostridium acetobuylicum* (Williams, *J Gen Microbiol,* 136: 819-826, 1990).

In certain embodiments having active restriction enzyme systems, it may be necessary to methylate a nucleic acid before introduction of the nucleic acid into the bacterium of the invention. A recombinant microorganism of the invention may be produced using a shuttle microorganism that facilitates the methylation of the DNA construct. For example, the shuttle microorganism may be restriction-negative *Escherichia coli, Bacillus* 27roduct27, or *Lactococcus lactis*. Methylation of the DNA construct may be achieved by introducing into a shuttle microorganism (i) a DNA construct to be introduced to a parental microorganism and (ii) a methylation construct/vector comprising a methyltransferase gene; expressing the methyltransferase gene; isolating the DNA construct from the shuttle microorganism; and introducing the DNA construct into the parental microorganism. The methylation construct/vector comprises a methyltransferase gene. Expression of the methyltransferase gene may be constitutive or induced. Induction may be by any suitable promoter, such as an inducible lac promoter that is induced by addition of lactose or an analogue thereof, such as isopropyl-β-D-thio-galactoside (IPTG). Other suitable promoters include the ara, tet, T7, PtRNA, PrRNA, Ppta/ack, or any transcriptionally active promoter that is inducible, conditional or constitutive. The methylation construct/vector may have an origin of replication specific to the identity of the shuttle microorganism so that any genes present on the methylation construct/vector are expressed in the shuttle microorganism. Expression of methyltransferase results in methylation of the genes present on the DNA construct, which can then be isolated from the shuttle microorganism using any method known in the art. In one embodiment, both the methylation construct/vector and the DNA constructs of the invention are concurrently isolated. Additionally or alternatively, a methyltransferase may be collected and used in vitro to methylate the DNA construct, which may then be introduced into the parental microorganism. In another embodiment, the methyltransferase gene is introduced into the genome of the shuttle microorganism followed by introduction of the DNA construct, isolation of the DNA construct from the shuttle microorganism, and introduction of the DNA construct into the parental microorganism. In one particular embodiment, the methylation construct/vector is a plasmid. The methyltransferase may be any methyltransferase known in the art. For example, the methyltransferase may be *Bacillus subtilis* phage ΦT1 methyltransferase or the methyltransferase described in WO 2012/053905. Moreover, any type of construct/vector known in the art may be used to generate the methylation construct/vector, including, for example, the methylation constructs/vectors described in WO 2012/053905.

A "microorganism" is a microscopic organism, especially a bacterium, archea, virus, or fungus. The microorganism of the invention is preferably a bacterium. As used herein, recitation of "microorganism" should be taken to encompass "bacterium."

The term "recombinant" indicates that a nucleic acid, protein, or microorganism is the product of genetic modification or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. In particular, the parental microorganism may be transformed with a DNA construct according to the methods of the present invention to produce a recombinant microorganism.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism.

The parental microorganism may be any type of microorganism, such as a bacterium, archea, virus, or fungus.

In one embodiment, the parental microorganism is an ABE bacterium, which is a Gram-positive Clostridial bacterium capable of producing butanol, ethanol, and acetone or isopropanol (see, e.g., Keis, *Int J Syst Evol Microbiol,* 51: 2095-2103, 2001). In one embodiment, the parental bacterium is and ABE bacterium selected from the group comprising

*Clostridium acetobutylicum*, *Clostridium beijerinckii*, *Clostridium saccharobutylicum*, and *Clostridium saccharoperbutylacetonicum*. In one embodiment, the parental microorganism is *Clostridium acetobutylicum* ATCC824 (DSM792) or EA 2018 (CCTCC M 94061). In another embodiment, the parental microorganism is *Clostridium beijerinckii* NCIMB8052 (ATCC51743) and NRRL B-593 (DSM 6423).

In one embodiment, the parental microorganism is an *Enterobacterium*, which is a rod-shaped, Gram-negative bacteria belonging to the order Enterobacteriacea and capable of fermenting sugars to produce lactic acid, ethanol, acetoin, 2,3-butabediol, and/or other products. In one embodiment, the parental bacterium is an *Enterobacterium* selected from the group comprising *Escherichia, Klebsiella, Zymomonas, Citrobacter, Enterobacter, Salmonella*, and *Serratia*. In one embodiment the parental microorganism is *Eschericia coli, Zymononas mobilis, Klebsiella pneumonia, Klebsiella oxtoca, Enterobacter cloacae*, or *Serratia marcescens*.

In one embodiment, the parental microorganism is a *Lactobacillus*, which is a gram-positive lactic acid bacterium belonging to the order Lactobacillales and capable of fermenting sugars to produce lactic acid, 2,3-butabediol, methyl ethyl ketone (MEK), 2-butanol, and/or other products. In one embodiment, the parental bacterium is a *Lactobacillus* selected from the group comprising *Lactobacillus, Lactococcus, Enterococcus, Pediococcus*, and *Streptococcus*. In one embodiment the parental microorganism is *Lactobacillus brevis, Enterococcus faecalis*, or *Lactococcus lactis*.

In one embodiment, the parental microorganism is a fungi or a yeast. Fungi are eukaryotic microorganisms, of which yeast are a specific subset, capable of fermenting sugars to produce ethanol, acetoin, and/or other products. In one embodiment, the parental microorganism is a fungi selected from the group comprising *Aspergillus, Trichoderma, Exophila, Mucor, Cladosporium, Phanerochaete, Cladiophilalophora, Paecilomyces, Scedosporium*, and *Ophistoma*. In one embodiment, the parental microorganism is *Aspargillus niger* or *Trichderma resei*. In one embodiment, the parental microorganism is a yeast selected from the group comprising *Saccharomyces, Pichia, Candida, Hansenula, Yarrowia, Rhodotorula, Rhizopus, Trichosporon, Lipomyces, Aspergillus, Trichoderma, Exophila, Mucor, Cladosporium, Phanerochaete, Cladiophilalophora, Paecilomyces, Scedosporium*, and *Ophistoma*. In one embodiment the parental microorganism is *Saccharomyces cerevisiae, Candidia tropicalis, Candidia albicans, Yarrowia lipolytica, Aspargillus niger*, or *Trichderma resei*.

In one embodiment, parental the microorganism is an aerobic carboxydotroph, which is a bacterium found ubiquitously in nature and isolated from various environments, including as humans (King, *Nat Rev Microbiol*, 5: 107-118, 2007). On taxonomic level, this physiological group is quite diverse, comprising of different phyla such as α-proteobacteria, firmicutes, or actinobacteria (King, *Nat Rev Microbiol*, 5: 107-118, 2007). All these organisms were shown to grown on CO levels >1% in presence of air (King, *Nat Rev Microbiol*, 5: 107-118, 2007). A typical gas mix consists of 50% CO and 50% air (Cypionka, *Appl Environ Microbiol*, 69: 1980-1989, 2003). In one embodiment, the parental microorganism is an aerobic carboxydotroph selected from the group comprising *Bacillus, Oligotropha, Pseudomonas, Carbophilus, Hydrogenophaga, Mycobacterium*, and *Zavarzinia*. In one embodiment, the parental microorganism is *Oligotropha carboxydovorans, Carbophilus carboxidus, Hydrogenophaga pseudoflava, Mycobacterium* sp., *Pseudomonas carboxydohydrogena, Pseudomonas* sp., *Zavarzinia compransoris*, or *Bacillus schlegelii*.

In one embodiment, the parental microorganism is an aerobic $CO_2$-fixing microorganism, which is a bacterium capable of fixing $CO_2$ with $H_2$ or via photosynthesis in presence of oxygen. The parental microorganism may be an aerobic $CO_2$-fixing microorganism selected from the group comprising *Cupravidus, Senechocystis*, and *Chloroflexus*. In one embodiment, the parental microorganism is *Cupravidus necator, Senechocystis* sp. or *Chloroflexus auranticus*.

In one embodiment, the parental microorganism is a methylotroph, which is a microorganism capable of using reduced one-carbon substrates, such as as methane or methanol, as carbon source for growth. The parental microorganism may be a methylotroph selected from the group comprising *Methylomonas, Methylobacter, Methylococcus, Methylomicrobium, Methylosphera, Methylocaldum, Methylocystis*, and *Methylosinus*. In one embodiment, the parental microorganism is *Methylococcus capsulatus* or *Methylosinus trichosporium*.

In one embodiment, the parental microorganism is a methanogen, which is an Archeae that capable of reducing $CO_2$ into methane. The parental microorganism may be a methanogen selected from the group comprising *Methanobacterium, Methanococcus, Methanogenium, Methanosarcina, Methanoshera, Methanothermobacter*, and *Methanotrix*. In one embodiment the parental microorganism is *Methanothermobacter marburgensis* or *Methanosarcina bakeri*.

In one embodiment, the parental microorganism is a carboxytroph, which is a microorganism capable of tolerating a high concentration of carbon monoxide (CO). In one embodiment, the parental microorganism is capable of using CO as a sole carbon and energy source. The parental microorganism may be selected from the cluster of carboxydotrophic Clostridia comprising the species *Clostridium autoethanogenum, Clostridium ljungdahlii, Clostridium ragsdalei*, and related isolates, including, but not limited to, strains *Clostridium autoethanogenum* JAI-1T (DSM10061) (Abrini, *Arch Microbiol*, 161: 345-351, 1994), *Clostridium autoethanogenum* LBS1560 (DSM19630) (WO 2009/064200), *Clostridium autoethanogenum* LZ1561 (DSM23693), *Clostridium ljungdahlii* PETCT (DSM13528=ATCC 55383) (Tanner, *Int J Syst Bacteriol*, 43: 232-236, 1993), *Clostridium ljungdahlii* ERI-2 (ATCC 55380) (U.S. Pat. No. 5,593,886), *Clostridium ljungdahlii* C-01 (ATCC 55988) (U.S. Pat. No. 6,368,819), *Clostridium ljungdahlii* 0-52 (ATCC 55989) (U.S. Pat. No. 6,368,819), *Clostridium ragsdalei* P11T (ATCC BAA-622) (WO 2008/028055), related isolates such as "*Clostridium coskatii*" (U.S. Publication 2011/0229947), or mutated strains such as *Clostridium ljungdahlii* OTA-1 (Tirado-Acevedo, Production of Bioethanol from Synthesis Gas Using *Clostridium ljungdahlii*, PhD thesis, North Carolina State University, 2010).

These strains form a subcluster within the Clostridial rRNA cluster I and their 16S rRNA gene is more than 99% identical with a similar low GC content of around 30%. However, DNA-DNA reassociation and DNA fingerprinting experiments showed that these strains belong to distinct species (WO 2008/028055). The strains of this cluster are defined by common characteristics, having both a similar genotype and phenotype, and they all share the same mode of energy conservation and fermentative metabolism. Furthermore, the strains of this cluster lack cytochromes and conserve energy via an Rnf complex. All species of this cluster have a similar morphology and size (logarithmic growing cells are between 0.5-0.7×3-5 μm), are mesophilic (optimal growth temperature between 30-37° C.), and are strictly anaerobic (Abrini, *Arch Microbiol,* 161: 345-351, 1994; Tanner, *Int J Syst Bacteriol,* 43: 232-236, 1993; and WO 2008/028055). Moreover, they all share the same major phylogenetic traits, such as same pH range (pH 4-7.5, with an optimal initial pH of 5.5-6), strong autotrophic growth on CO-containing gases with similar growth rates, and a similar metabolic profile with ethanol and acetic acid as main fermentation end products, and small amounts of 2,3-butanediol and lactic acid formed under certain conditions (Abrini, *Arch Microbiol,* 161: 345-351, 1994; Kopke, *Curr Opin Biotechnol,* 22: 320-325, 2011; Tanner, *Int J Syst Bacteriol,* 43: 232-236, 1993; and WO 2008/028055). Indole production was observed with all three species as well.

However, the species differentiate in substrate utilization of various sugars (e.g., rhamnose, arabinose), acids (e.g., gluconate, citrate), amino acids (e.g., arginine, histidine), or other substrates (e.g., betaine, butanol). Moreover some of the species were found to be auxotrophic to certain vitamins (e.g., thiamine, biotin) while others were not. The organization and number of Wood-Ljungdahl pathway genes, responsible for gas uptake, has been found to be the same in all species, despite differences in nucleic and amino acid sequences (Kopke, *Curr Opin Biotechnol*, 22: 320-325, 2011). Also, reduction of carboxylic acids into their corresponding alcohols has been shown in a range of these microorganisms (Perez, *Biotechnol Bioeng*, 110:1066-1077, 2012). These traits are therefore not specific to one microorganism, like *Clostridium autoethanogenum* or *Clostridium ljungdahlii*, but rather general traits for carboxydotrophic, ethanol-synthesizing Clostridia and it can be anticipated that mechanisms work similarly across these strains, although there may be differences in performance.

In one embodiment, the parental microorganism is selected from genus *Clostridium, Acetobacterium, Moorella, Butyribacterium, Blautia, Oxobacter, Thermoanaerobacter, Escherichia, Klebsiella, Zymomonas, Citrobacter, Enterobacter, Salmonella, Serratia, Lactobacillus, Lactococcus, Enterococcus, Pediococcus, Streptococcus, Saccharomyces, Pichia, Candida Hansenula, Yarrowia, Rhodotorula, Rhizopus, Trichosporon, Lipomyces, Aspergillus, trichoderma, Exophila, Mucor, Cladosporium, Phanerochaete, Cladiophilalophora, Paecilomyces, Scedosporium, Ophistoma, Bacillus, Oligotropha, Pseudomonas, Carbophilus, Hydrogenophaga, Mycobacterium, Zavarzinia, Cupravidus, Senechocystis, Chloroflexus, Methylomonas, Methylobacter, Methylococcus, Methylomicrobium, Methylosphera, Methylocaldum, Methylocystis, Methylosinus, Methanobacterium, Methanococcus, Methanogenium, Methanosarcina, Methanoshera, Methanothermobacter, Methanotrix, Corynebacterium, Acinetobacter, Actinomyces, Bacteroides, Burkholderia, Brevibacterium, Pyrococcus, Geobacter, Geobacillus, Paenibacillus, Mycobacterium, Rhodopseudomonas, Thermatoga, Thermoanaerobacter, Streptomyces, Rhodobacter, Rhodococcus, Peptococcus, Bifidobacterium, Propionibacterium, Fusobacterium, Campylobacter, Veillonella, Aquincola, Arthrobacter, Moraxella*, or *Psychrobacter.*

In one embodiment, the parental microorganism is a carboxydotrophic acetogenic bacterium. An acetogen is a microorganism that generates or is capable of generating acetate as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta,* 1784: 1873-1898, 2008). The parental microorganism may be a carboxydotrophic acetogenic bacterium selected from the group comprising *Clostridium autoethanogenum, Clostridium ljungdahlii, Clostridium ragsdalei, Clostridium carboxidivorans, Clostridium drakei, Clostridium scatologenes, Clostridium coskatii, Clostridium aceticum, Clostridium magnum, Clostridium* sp., *Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii*, and *Thermoanaerobacter kiuvi*. In a preferred embodiment, the parental microorganism is *Clostridium autoethanogenum* deposited under DSMZ accession DSM10061, *Clostridium autoethanogenum* deposited under DSMZ accession DSM13528 (ATTC 55383), or *Clostridium autoethanogenum* deposited under DSMZ accession DSM23693 (known as *Clostridium autoethanogenum* LZ1561).

The microorganism of the invention may be cultured to produce one or more products, such as ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152).

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the bacterium. Preferably the aqueous culture medium is a minimal anaerobic microbial growth medium. The medium may also be Clostridia minimal medium, minimal defined medium (MDM), supplemented defined medium (SDM), or complete defined medium (CDM). The medium may be PETC medium. Suitable media are known in the art and described, for example, in U.S. Pat. No. 5,173,429, U.S. Pat. No. 5,593,886, and WO 2002/008438.

The culture/fermentation should desirably be carried out under appropriate conditions for production of the target product. Reaction conditions to consider include pressure, temperature, gas flow rate, liquid flow rate, media pH, media redox potential, agitation rate (if using a continuous stirred tank reactor), inoculum level, maximum substrate concentrations, and maximum product concentrations.

The term "substrate" refers to a carbon and/or energy source for the microorganism of the invention. The type of substrate required will depend on the nature of the microorganism. The substrate may comprise a gas, such as CO, $CO_2$, $H_2$, $O_2$, and/or $N_2$. The substrate may comprise a carbohydrate, such as glucose, fructose, lignocellulose, cellulose, or starch.

EXAMPLES

The following examples further illustrate the invention but, of course, should not be construed to limit its scope in any way.

Example 1

This example describes general materials and methods.

*C. autoethanogenum* DSM10061 and DSM23693 (a derivate of DSM10061) and *C. ljungdahlii* DSM13528 were sourced from DSMZ (The German Collection of Microorganisms and Cell Cultures, Inhoffenstraβe 7 B, 38124 Braunschweig, Germany). *C. ragsdalei* ATCC BAA-622 was sourced from ATCC (American Type Culture Collection, Manassas, Va. 20108, USA). *E. coli* DH5α was sourced from Invitrogen (Carlsbad, Calif. 92008, USA).

*E. coli* was grown aerobic at 37° C. in LB (Luria-Bertani) medium. Solid media contained 1.5% agar.

| LB medium component | Amount per 1.0 L of LB medium |
|---|---|
| Tryptone | 10 g |
| Yeast extract | 5 g |
| NaCl | 10 g |

*Clostridium* strains were grown at 37° C. in PETC medium at pH 5.6 using standard anaerobic techniques (Hungate, *Methods Microbiol,* 3B: 117-132, 1969; Wolfe, *Adv Microbiol Physiol,* 6: 107-146, 1971). Fructose (heterotrophic growth) or 30 psi CO-containing steel mill gas (collected from New Zealand Steel site in Glenbrook, NZ; composition: 44% CO, 32% $N_2$, 22% $CO_2$, 2% $H_2$) in the headspace (autotrophic growth) was used as substrate. For solid media, 1.2% bacto agar (BD, Franklin Lakes, N.J. 07417, USA) was added.

| PETC medium component | Amount per 1.0 L of PETC medium |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution (see below) | 10 ml |
| Wolfe's vitamin solution (see below) | 10 ml |
| Yeast extract (optional) | 1 g |
| Resazurin (2 g/L stock) | 0.5 ml |
| $NaHCO_3$ | 2 g |
| Reducing agent solution (see below) | 0.006-0.008% (v/v) |
| Fructose (for heterotrophic growth) | 5 g |

| Trace metal solution component | Amount per 1.0 L of trace metal solution |
|---|---|
| Nitrilotriacetic acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |

| Wolfe's vitamin solution component | Amount per 1.0 L of Wolfe's vitamin solution |
|---|---|
| Biotin | 2 mg |
| Folic acid | 2 mg |
| Pyridoxine hydrochloride | 10 mg |
| Thiamine HCl | 5 mg |
| Riboflavin | 5 mg |
| Nicotinic acid | 5 mg |
| Calcium D-(+)-pantothenate | 5 mg |
| Vitamin B12 | 0.1 mg |
| P-aminobenzoic acid | 5 mg |
| Thioctic acid | 5 mg |

| Reducing agent solution component | Amount per 100 mL of reducing agent solution |
|---|---|
| NaOH | 0.9 g |
| Cysteine-HCl | 4 g |
| $Na_2S$ | 4 g |

Example 2

This example demonstrates in-frame gene deletion or gene insertion into the genome of *C. autoethanogenum.*

In-frame deletion or insertion of a gene into the genome of *C. autoethanogenum* was achieved using an embodiment of the invention comprising the use of two counter selection markers, two selection steps, and three homologous-mediated crossover events.

Figure 12:
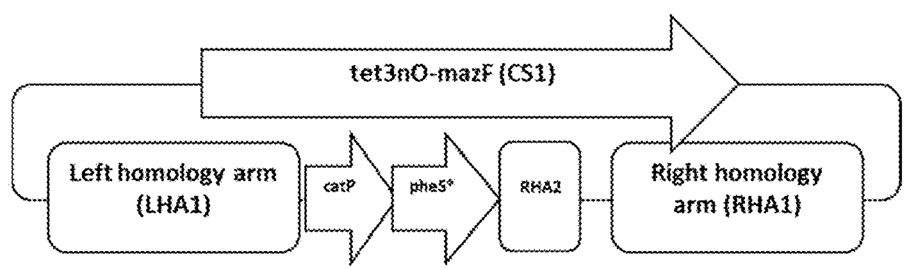
FIG. 12 is a diagram showing TXp3 plasmid features.
Figure 13:
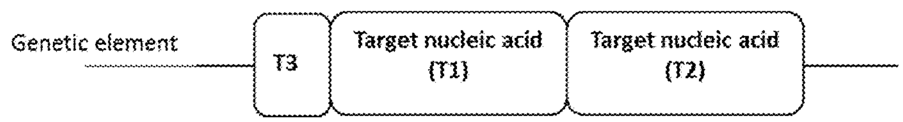
FIG. 13 is a diagram showing genome organization for use with a DNA construct such as a TXp3 plasmid.
Figure 14:
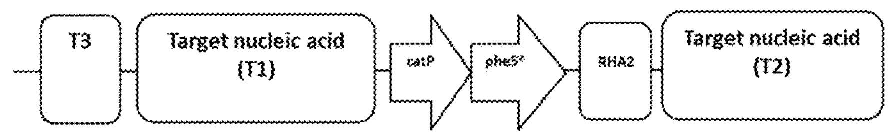
FIG. 14 is a diagram showing a double crossover recombination genotype.
Figure 17:
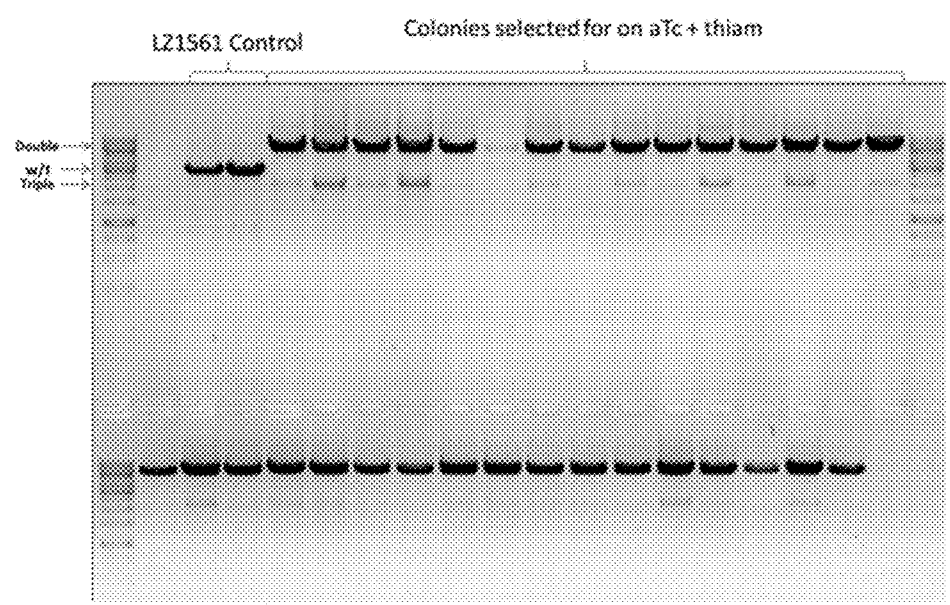
FIG. 17 is a gel image showing the results of screening double crossover recombinants using plasmid TXp3.

FIG. 12 shows the DNA construct (TXp3 plasmid) comprising CS1 (tet3nO-mazF), LHA1, catP, pheS*, RHA2, and RHA1. FIG. 13 shows the organization of a genetic element in the genome of *C. autoethanogenum*. Homology arms LHA1 and RHA1 were designed to recombine with T1 and T2, respectively, to integrate the DNA between LHA1 and RHA1 into the genome of *C. autoethanogenum* between T1 and T2. By selecting for the positive selection marker (catP) and against the counter selection marker 1 (tet3nO-mazF), the desired double crossover recombination event was selected for with very high efficiency (FIG. 14 and FIG. 17).

Figure 15:
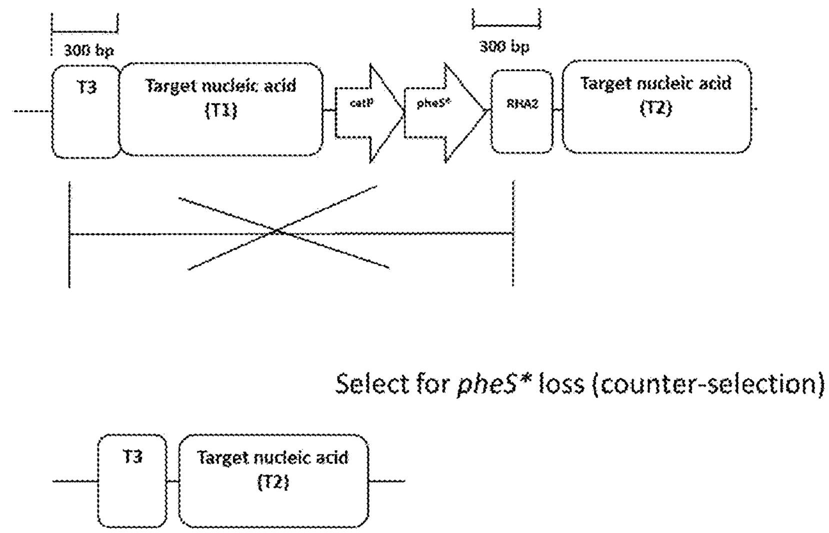
FIG. 15 is a diagram showing a triple crossover recombination genotype.

Once the double crossover mutant was purified and enriched, T3 was allowed to recombine with RHA2 to delete target gene T1. Selection for the recombination event between T3 and RHA2 was performed by selecting against CS2 (selecting against pheS* by the addition of chlorophenylalanine) (FIG. 15).

Figure 16:
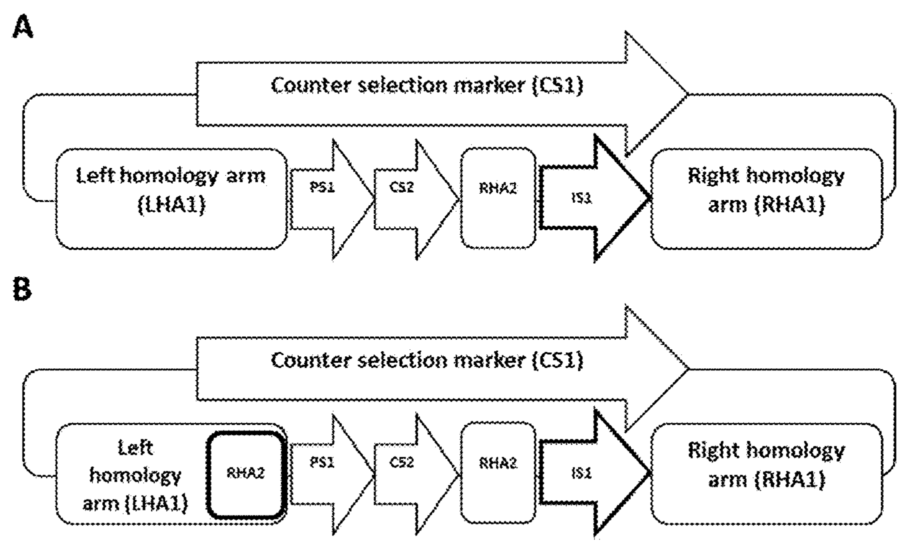
FIG. 16 is a set of diagrams showing example plasmid architecture for allelic replacement (A) and DNA insertion (B).

This system can be modified to allelic replace (A) or insert (B) DNA into the genome of *C. autoethanogenum* depending on the position of the RHA2 homology arm (FIG. 16).

Example 3

This example demonstrates the deletion of a 2,3-butanediol dehydrogenase (2,3-BDH) gene (SEQ ID NO: 9) of *C. autoethanogenum* LZ1561.

pheS* (SEQ ID NO: 1) was used as a counter selection marker on the backbone of the DNA construct and tet3nO-mazF (SEQ ID NO: 6) used as a counter selection marker between the LHA1 (SEQ ID NO: 7) and RHA2 (SEQ ID NO: 8) homology arms. The DNA construct was synthesized and then transformed into *C. autoethanogenum* LZ1561 via conjugation. For this, the expression vector was first introduced into the conjugative donor strain *E. coli* CA434 (the "donor") using standard heat shock transformation. Donor cells were recovered in SOC medium at 37° C. for 1 h before being plated on to LB plates containing 100 μg/ml spectinomycin and 25 μg/ml chloramphenicol. LB plates were incubated at 37° C. overnight. The next day, 5 ml LB aliquots containing 100 μg/ml spectinomycin and 25 μg/ml chloramphenicol were inoculated with several donor colonies and incubated at 37° C., shaking for approximately 4 h, or until the culture was visibly dense but had not yet entered stationary phase. 1.5 ml of the donor culture was harvested in a microcentrifuge tube at room temperature by centrifugation at 4000 rpm for 2 min, and the supernatant was discarded. The donor cells were gently resuspended in 500 μl sterile PBS and centrifuged at 4000 rpm for 2 min and the PBS supernatant was discarded. The pellet was introduced into an anaerobic chamber and gently resuspended in 200 μl during late exponential phase *C. autoethanogenum* culture (the "recipient"). The conjugation mixture (the mix of donor and recipient cells) was spotted onto PETC-MES+fructose agar plates and left to dry. When the spots were no longer visibly wet, the plates were introduced into a pressure jar, pressurized with syngas to 25-30 psi and incubated at 37° C. for ~24 h. After 24 h incubation, the conjugation mixture was removed from the plates by gently scraping it off using a 10 μl inoculation loop. The removed mixture was suspended in 200-300 μl PETC-MES. 100 μl aliquots of the conjugation mixture were plated on to PETC-MES agar plates supplemented 15 μg/ml thiamphenicol to select for catP and 10 μg/ml trimethoprim and by the addition of 31 ng/ml anhydrous tetracycline to induce mazF expression and select for the double crossover. Plates were reintroduced into the pressure jar, pressurized to 25-30 psi of syngas, and incubated at 37° C. for 3-4 days. After this single-step counter selection of tet3nO-mazF and positive selection of catP, double crossover integrants were identified in the 16 integrants analyzed.

Using a set of primers to amplify across the 2,3-BDH site, it was shown that double and triple crossover recombination happens at high enough frequency to be isolated with the correct counter selection. The positive control was a colony previously shown to be a pure Δ2,3-BDH strain identified via traditional double crossover homologous recombination by screening a high number of colonies.

In some cases triple crossover (and subsequently deletion of 2,3-BDH) was already observed for part of the population at this first step (FIG. 17). By further subculturing the triple crossover step would occur (without the need for a second selection step).

To select for the triple crossover recombination and subsequently deletion of 2,3-BDH, the strain was plated onto chlorophenylalanine selecting for the triple crossover recombination with the second negative marker pheS* with subsequent deletion of the 2,3-BDH. To screen for the absence of the plasmid, primers against the Gram-negative origin ColE1 were used. To screen for the positive triple cross gene deletion, a screen with primers in the homology arms was performed to confirm the correct size for the deleted gene.

To select for the triple crossover recombination and subsequently deletion of 2,3-BDH) in a second step, the strain was plated onto 2 g/L chlorophenylalanine selecting for the triple crossover recombination with the second negative marker pheS*. To screen for the absence of the plasmid, primers against the Gram-negative origin ColE1 were used. To screen for the positive triple cross gene deletion, a screen with primers in the homology arms was performed to confirm the correct size for the deleted gene.

Sequencing confirmed the successful, scar-less deletion of the 2,3-butanediol gene. Nucleotide sequences of the respective genomic region in *C. autoethanogenum* LZ1561 (SEQ ID NO: 10), the double crossover (SEQ ID NO: 11), and triple crossover (SEQ ID NO: 12) are provided.

The same procedure has also been successfully applied to knock out the secondary alcohol dehydrogenase gene of *C. autoethanogenum* (SEQ ID NO: 13).

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing a recombinant microorganism, comprising:

(a) providing a microorganism comprising a genetic element comprising target nucleic acid T1, a target nucleic acid T2, and a target nucleic acid T3, (b) providing a DNA construct comprising a left homology arm LHA1 homologous to T1, a right homology arm RHA1 homologous to T2, and a right homology arm RHA2 homologous to T3, wherein RHA2 is located between LHA1 and RHA1, (c) allowing the genetic element of (a) to undergo homologous recombination with the DNA construct of (b), whereby T1 aligns with LHA1 and T2 aligns with RHA1 to insert the portion of the DNA construct between LHA1 and RHA1, including RHA2, into the genetic element between T1 and T2, and (d) allowing the genetic element of (c) to undergo self-homologous recombination, whereby T3 aligns with RHA2 to remove the portion of the genetic element between T3 and RHA2.

2. The method of claim 1, wherein the genetic element of (a) comprises 5'-T3-T1-T2-3'; the DNA construct of (b) comprises 5'-LHA1-RHA2-RHA1-3'; a microorganism comprising a genetic element comprising 5'-T3-T1-RHA2-T2-3' is formed in (and a microorganism comprising a genetic element comprising 5'-T3-T2-3' is formed in (d) such that T1 is deleted from the genetic element.

3. The method of claim 1, wherein the genetic element of (a) comprises 5'-T3-T1-T2-3'; the DNA construct of (b) comprises 5'-LHA1-RHA2-IS1-RHA1-3' wherein IS1 is an insertion nucleic acid; a microorganism comprising a genetic element comprising 5'-T3-T1-RHA2-IS1-T2-3' is formed in (c); and a microorganism comprising a genetic element comprising 5'-T3-IS1-T2-3' is formed in (d), such that T1 is replaced IS1 in the genetic, element.

4. The method of claim 1, wherein the genetic element of (a) comprises 5'-T1$_{T3}$-3-T4-T2-3' wherein T1 encompasses T3 and T4 is a target nucleic acid; the DNA construct of (b) comprises 5'-LHA1$_{RHA2}$-RHA2-RHA1-3 wherein LHA1 encompasses RHA2; a microorganism comprising a genetic element comprising 5'-T1$_{T3}$-RHA2-T2-3' is formed in (c); and a microorganism comprising a genetic element comprising 5'-T1$_{T3}$-T2-3' is formed in (d), such that T4 is deleted from the genetic element.

5. The method of claim 1, wherein the genetic element of (a) comprises 5'-T1$_{T3}$-T2-3' wherein T1 encompasses T3; the DNA construct of (b) comprises 5'-LHA1$_{RHA2}$-RHA2-IS1-RHA1-3' wherein LHA1 encompasses RHA2 and IS1 is an insertion nucleic acid; a microorganism comprising a genetic element comprising 5'-T1$_{T3}$-RHA2-IS1-T2-3' is formed in (c); and a microorganism comprising a genetic element comprising 5'-T1$_{T3}$-IS1-T2-3' is formed in (d), such that IS 1 is inserted in the genetic element.

6. The method of claim 1, wherein the genetic element of (a) comprises 5'-T1$_{T3}$-T4-T2-3' wherein T1 encompasses T3 and T4 is a target nucleic acid; the DNA construct of (b) comprises 5'-LHA1$_{RHA2}$-RHA2-IS1-RHA1-3 wherein LHA1 encompasses RHA2 and IS1 is an insertion nucleic acid; a microorganism comprising a genetic element comprising 5'-T1$_{T3}$-RHA2-IS1-T2-3' is formed in (c); and a microorganism comprising a genetic element comprising 5'-T1$_{T3}$-IS1-T2-3' is formed in (d), such that T4 is replaced by IS1 in the genetic element.

7. The method of claim 1, wherein the DNA construct of (b) further comprises a counter selection marker CS1 upstream of LHA1 and a positive selection marker PS1 and a counter selection marker CS2 between LHA1 and RHA2.

8. The method of claim 7, wherein (c) is followed by a step of selecting for expression of PS1 and against expression of CS1 and (d) is followed by a step of selecting against expression of CS2.

9. The method of claim 7, wherein CS1 and CS2 are independently selected from the group consisting of pheS*, upp, sacB, tetAR, thyA, ccdB, lacY, rpsL, codA, pyrE, HSTK (thiK) gatA-1, and mazF; and PS1 is selected from the group consisting of catP, tetA(C), tetM, aad9, aadA, aadA2, and ermB.

10. The method of claim 1, wherein the DNA construct of (b) further comprises a counter selection marker CS1 upstream of LHA1 and a positive selection marker PS1 between LHA1 and RHA2.

11. The method of claim 10, wherein is followed by a step of selecting for expression of PS1 and against expression of CS1.

12. The method of claim 10, wherein CS1 is selected from the group consisting of pheS*, upp, sacB, tetAR, thyA, ccdB, lacY, rpsL, codA, pyrE, HSTK (thiK), gatA-1, and mazF; and PS1 is selected from the group consisting of catP, tetA(C), tetM, aad9, aadA, aadA2, and ermB.

13. The method of claim 1, wherein LHA1 is longer than RHA2.

14. The method of claim 13, wherein LHA1 is equal to or greater than about 1000 base pairs in length and RHA2 is equal to or less than about 300 base pairs in length.

15. The method of claim 1, wherein LHA1 and RHA1 are each longer than RHA2.

16. The method of claim 15, wherein LHA1 and RHA1 are each equal to or greater than about 1000 base pairs in length and RHA2 is equal to or less than about 300 base pairs in length.

17. The method of claim 1, wherein the microorganism is a bacterium, archea, virus, or fungus.

18. The method of claim 1, wherein the microorganism belongs to genus *Clostridium, Acetobacterium, Moorella, Butyribacterium, Blautia, Oxobacter, Thermoanaerobacter, Escherichia, Klebsiella, Zymomonas, Citrobacter, Enterobacter, Salmonella, Serratia, Lactobacillus, Lactococcus, Enterococcus, Pediococcus, Streptococcus, Saccharomyces, Pichia, Candida Hansenula, Yarrowia, Rhodotorula, Rhizopus, Trichosporon, Lipomyces, Aspergillus, trichoderma, Exophila, Mucor, Cladosporium, Phanerochaete, Cladiophilalophora, Paecilomyces, Scedosporium, Ophistoma, Bacillus, Oligotropha, Pseudomonas, Carbophilus, Hydrogenophaga, Mycobacterium, Zavarzinia, Cupravidus, Senechocystis, Chloroflexus, Methylomonas, Methylobacter,*

*Methylococcus, Methylomicrobium, Methylosphera, Methylocaldum, Methylocystis, Methylosinus, Methanobacterium, Methanococcus, Methanogenium, Methanosarcina, Methanoshera, Methanothermobacter, Methanotrix, Corynebacterium, Acinetobacter, Actinomyces, Bacteroides, Burkholderia, Brevibacterium, Pyrococcus, Geobacter, Geobacillus, Paenibacillus, Mycobacterium, Rhodopseudomonas, Thermatoga, Thermoanaerobacter, Streptomyces, Rhodobacter, Rhodococcus, Peptococcus, Bifidobacterium, Propionibacterium, Fusobacterium, Campylobacter, Veillonella, Aquincola, Arthrobacter, Moraxella*, or *Psychrobacter.*

* * * * *